United States Patent
Stupp et al.

(10) Patent No.: US 11,066,444 B2
(45) Date of Patent: Jul. 20, 2021

(54) BMP-2-BINDING PEPTIDE AMPHIPHILE NANOFIBERS

(71) Applicant: Northwestern University, Evanston, IL (US)

(72) Inventors: Samuel I. Stupp, Chicago, IL (US); Erin L. Hsu, Glenview, IL (US); Wellington K. Hsu, Glenview, IL (US); Sungsoo Lee, Chicago, IL (US)

(73) Assignee: Northwestern University, Evanston, IL (US)

( * ) Notice: Subject to any disclaimer, the term of this patent is extended or adjusted under 35 U.S.C. 154(b) by 9 days.

(21) Appl. No.: 16/533,253

(22) Filed: Aug. 6, 2019

(65) Prior Publication Data

US 2020/0140486 A1 May 7, 2020

Related U.S. Application Data

(63) Continuation of application No. 14/963,847, filed on Dec. 9, 2015, now abandoned.

(60) Provisional application No. 62/089,560, filed on Dec. 9, 2014.

(51) Int. Cl.
| | |
|---|---|
| *A61K 38/02* | (2006.01) |
| *C07K 14/51* | (2006.01) |
| *C07K 7/02* | (2006.01) |
| *A61K 38/00* | (2006.01) |
| *C07K 7/06* | (2006.01) |
| *A61K 47/54* | (2017.01) |
| *B82Y 40/00* | (2011.01) |
| *B82Y 5/00* | (2011.01) |
| *B82Y 30/00* | (2011.01) |

(52) U.S. Cl.
CPC ............... *C07K 7/06* (2013.01); *A61K 38/00* (2013.01); *A61K 47/542* (2017.08); *C07K 14/51* (2013.01); *B82Y 5/00* (2013.01); *B82Y 30/00* (2013.01); *B82Y 40/00* (2013.01); *C07K 2319/00* (2013.01)

(58) Field of Classification Search
CPC ....... A61K 38/1875; A61K 38/02; C07K 7/02
See application file for complete search history.

(56) References Cited

U.S. PATENT DOCUMENTS

| | | | |
|---|---|---|---|
| 6,890,654 B2 | 5/2005 | Stupp et al. | |
| 7,371,719 B2 | 5/2008 | Stupp et al. | |
| 7,390,526 B2 | 6/2008 | Stupp et al. | |
| 7,452,679 B2 | 11/2008 | Stupp et al. | |
| 7,491,690 B2 | 2/2009 | Stupp et al. | |
| 7,534,761 B1 | 5/2009 | Stupp et al. | |
| 7,544,661 B2 | 6/2009 | Stupp et al. | |
| 7,554,021 B2 | 6/2009 | Stupp et al. | |
| 7,683,025 B2 | 3/2010 | Stupp et al. | |
| 7,745,708 B2 | 6/2010 | Stupp et al. | |
| 7,838,491 B2 | 11/2010 | Stupp et al. | |
| 7,851,445 B2 | 12/2010 | Stupp et al. | |
| 8,063,014 B2 | 11/2011 | Stupp et al. | |
| 8,080,262 B2 | 12/2011 | Stupp et al. | |
| 8,114,834 B2 | 2/2012 | Stupp et al. | |
| 8,114,835 B2 | 2/2012 | Stupp et al. | |
| 8,124,583 B2 | 2/2012 | Stupp et al. | |
| 8,138,140 B2 | 3/2012 | Stupp et al. | |
| 8,450,271 B2 | 5/2013 | Shah et al. | |
| 8,512,693 B2 | 8/2013 | Capito et al. | |
| 2005/0209145 A1* | 9/2005 | Stupp .................. | A61P 19/02 514/8.1 |
| 2009/0098652 A1* | 4/2009 | Stupp .................. | C12N 15/87 435/455 |
| 2013/0017228 A1* | 1/2013 | Davis .................. | A61K 35/33 424/400 |
| 2014/0017211 A1* | 1/2014 | Edinger .............. | A61P 19/08 424/93.7 |

OTHER PUBLICATIONS

Hoffmann et al. (2012) "Recombinant Human Bone Morphogenetic Protein-2 (rhBMP-2) in Posterolateral Spinal Fusion: What's the Right Dose?" ORS 2012 Anuual meeting, Poster, p. 1.*
Girard et al. (2014) Post-traumatic lower cervical spine instability: Arthrodesis clinical and radiological outcomes at 5 years, Orthopaed. Traumatol. Surgery Res., vol. 100, pp. 385-388.*
Aghdasi et al. A review of demineralized bone matrices for spinal fusion: the evidence for efficacy. Surgeon. Feb. 2013;11(1):39-48.
Angeloni et al. Regeneration of the cavernous nerve by Sonic hedgehog using aligned peptide amphiphile nanofibers. Biomaterials. Feb. 2011;32(4):1091-101.
Aro et al. Recombinant human bone morphogenetic protein-2: a randomized trial in open tibial fractures treated with reamed nail fixation. J Bone Joint Surg Am. May 4, 2011;93(9):801-8.
Behanna et al. Coassembly of amphiphiles with opposite peptide polarities into nanofibers.J Am Chem Soc. Feb. 2, 2005;127(4):1193-200.
Benoit et al. Multifunctional hydrogels that promote osteogenic hMSC differentiation through stimulation and sequestering of BMP2. Adv Funct Mater. 2007;17(13):2085-2093.
Boekhoven et al. Programmed morphological transitions of multisegment assemblies by molecular chaperone analogues.Angew Chem Int Ed Engl. Dec. 16, 2011;50(51):12285-9.
Bramono et al. Bone marrow-derived heparan sulfate potentiates the osteogenic activity of bone morphogenetic protein-2 (BMP-2). Bone. Apr. 2012;50(4):954-64.
Brower & Vickroy, A case of psoas ossification from the use of BMP-2 for posterolateral fusion at L4-L5. Spine (Phila Pa 1976). Aug. 15, 2008;33(18):E653-5.

(Continued)

*Primary Examiner* — Scarlett Y Goon
*Assistant Examiner* — Samuel W Liu
(74) *Attorney, Agent, or Firm* — Casimir Jones SC; David W. Staple

(57) ABSTRACT

Provided herein are peptide amphiphiles with binding affinity for the bone promoting growth factor BMP-2, and methods of use thereof. In particular nanofibers and gel scaffolds of BMP-2-binding peptide amphiphiles are provided.

9 Claims, 28 Drawing Sheets

Specification includes a Sequence Listing.

(56) References Cited

OTHER PUBLICATIONS

Capila et al. Heparin-protein interactions. Angew Chem Int Ed Engl. Feb. 1, 2002;41(3):391-412.
Ghanaati et al. Dynamic in vivo biocompatibility of angiogenic peptide amphiphile nanofibers. Biomaterials 2009, 30(31):6202-6212.
Hartgerink et al. Self-assembly and mineralization of peptide-amphiphile nanofibers. Science. Nov. 23, 2001;294(5547):1684-8.
Hsu et al. Characterizing the host response to rhBMP-2 in a rat spinal arthrodesis model. Spine (Phila Pa 1976). May 20, 2013;38(12):E691-8.
Hsu et al. Improving the Clinical Evidence of Bone Graft Substitute Technology in Lumbar Spine Surgery. Global Spine J. Dec. 2012; 2(4):239-248.
Hsu et al. Nanocomposite therapy as a more efficacious and less inflammatory alternative to bone morphogenetic protein-2 in a rodent arthrodesis model. J Orthop Res. Dec. 2011;29(12):1812-9.
Hsu et al. Stem cells from human fat as cellular delivery vehicles in an athymic rat posterolateral spine fusion model. J Bone Joint Surg Am. May 2008;90(5):1043-52.
Huang et al. Biological synthesis of tooth enamel instructed by an artificial matrix. Biomaterials. Dec. 2010;31(35):9202-11.
Hudalla & Murphy, Biomaterials that regulate growth factor activity via bioinspired interactions. Adv Funct Mater. May 24, 2011;21(10):1754-1768.
Jiao et al. Heparan sulfate proteoglycans (HSPGs) modulate BMP2 osteogenic bioactivity in C2C12 cells. J Biol Chem. Jan. 12, 2007;282(2):1080-6.
Knecht et al. Oligohis-tags: mechanisms of binding to Ni2+–NTA surfaces. J Mol Recognit. Jul.-Aug. 2009;22(4):270-9.
Kuo et al. Heparan sulfate acts as a bone morphogenetic protein coreceptor by facilitating ligand-induced receptor hetero-oligomerization. Mol Biol Cell. Nov. 15, 2010;21(22):4028-41.
Latham & Lau, Bone Stimulation: A Review of Its Use as an Adjunct. Techniques in Orthopaedics Mar. 2011; 26(1):14-21.
Lee et al. Bone regeneration with low dose BMP-2 amplified by biomimetic supramolecular nanofibers within collagen scaffolds. Biomaterials. Jan. 2013;34(2):452-9.
Lee et al. Growth factor delivery-based tissue engineering: general approaches and a review of recent developments. J R Soc Interface. Feb. 6, 2011;8(55):153-70.
Lutolf et al. Designing materials to direct stem-cell fate. Nature. Nov. 26, 2009;462(7272):433-41.
Mata et al. Bone regeneration mediated by biomimetic mineralization of a nanofiber matrix. Biomaterials. Aug. 2010;31(23):6004-12.
Matson et al. Peptide Self-Assembly for Crafting Functional Biological Materials. Curr Opin Solid State Mater Sci. Dec. 2011;15(6):225-235.
Morgan et al. Synergistic control of cell adhesion by integrins and syndecans. Nat Rev Mol Cell Biol. Dec. 2007;8(12):957-69.
Muchow et al. Histopathologic inflammatory response induced by recombinant bone morphogenetic protein-2 causing radiculopathy after transforaminal lumbar interbody fusion. Spine J. Sep. 2010;10(9):e1-6. doi: 10.1016/j.spinee.2010.06.020.
Murali et al. Affinity-selected heparan sulfate for bone repair. Biomaterials. Jul. 2013;34(22):5594-605.
Pashuck et al. Designing regenerative biomaterial therapies for the clinic. Sci Transl Med. Nov. 14, 2012;4(160):160sr4.
Pashuck et al. Tuning supramolecular rigidity of peptide fibers through molecular structure.J Am Chem Soc. May 5, 2010;132(17):6041-6.
Peterson et al. Osteoinductivity of commercially available demineralized bone matrix. Preparations in a spine fusion model. J Bone Joint Surg Am. Oct. 2004;86-A(10):2243-50.
Rajangam et al. Heparin binding nanostructures to promote growth of blood vessels. Nano Lett. Sep. 2006;6(9):2086-90.
Rajangam et al. Peptide amphiphile nanostructure-heparin interactions and their relationship to bioactivity. Biomaterials. Aug. 2008;29(23):3298-305.
Reddi, Role of morphogenetic proteins in skeletal tissue engineering and regeneration. Nat Biotechnol. Mar. 1998;16(3):247-52.
Sargeant et al. Hybrid bone implants: self-assembly of peptide amphiphile nanofibers within porous titanium. Biomaterials. Jan. 2008;29(2):161-71.
Shah et al. Supramolecular design of self-assembling nanofibers for cartilage regeneration. Proc Natl Acad Sci U S A. Feb. 23, 2010;107(8):3293-8.
Shah et al. Surface-mediated bone tissue morphogenesis from tunable nanolayered implant coatings. Sci Transl Med. Jun. 26, 2013;5(191):191ra83.
Tysseling-Mattiace et al. Self-assembling nanofibers inhibit glial scar formation and promote axon elongation after spinal cord injury. J Neurosci. Apr. 2, 2008;28(14):3814-23.
Uludag et al. Implantation of recombinant human bone morphogenetic proteins with biomaterial carriers: A correlation between protein pharmacokinetics and osteoinduction in the rat ectopic model. J Biomed Mater Res. May 2000;50(2):227-38.
Vaidya et al. Complications in the use of rhBMP-2 in PEEK cages for interbody spinal fusions. J Spinal Disord Tech. Dec. 2008;21(8):557-62.
Webber et al. Development of bioactive peptide amphiphiles for therapeutic cell delivery. Acta Biomater. Jan. 2010;6(1):3-11.
Webber et al. Supramolecular nanostructures that mimic VEGF as a strategy for ischemic tissue repair. Proc Natl Acad Sci U S A. Aug. 16, 2011;108(33):13438-43.
Willie et al. Designing biomimetic scaffolds for bone regeneration: why aim for a copy of mature tissue properties if nature uses a different approach? Soft Matter, Aug. 2010; 6:4976-4987.
Wong et al. Neurologic impairment from ectopic bone in the lumbar canal: a potential complication of off-label PLIF/TLIF use of bone morphogenetic protein-2 (BMP-2). Spine J. Nov.-Dec. 2008;8(6):1011-8.
Zhao et al. Heparin potentiates the in vivo ectopic bone formation induced by bone morphogenetic protein-2. J Biol Chem. Aug. 11, 2006;281(32):23246-53.

* cited by examiner carboxyl-rich domain

FIG. 10A
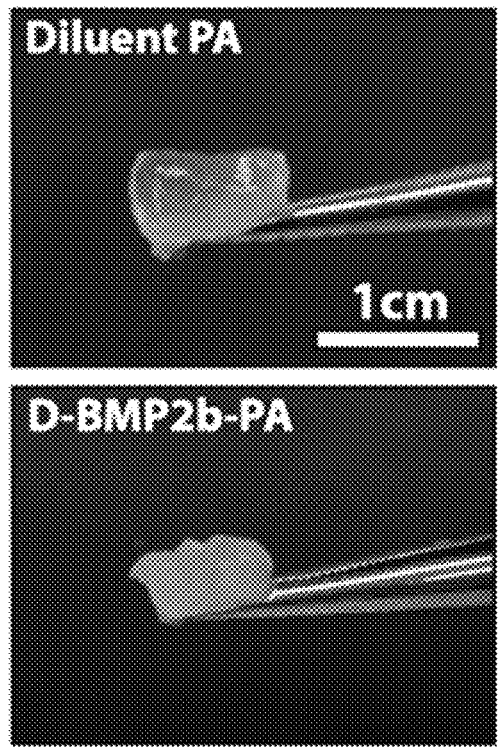
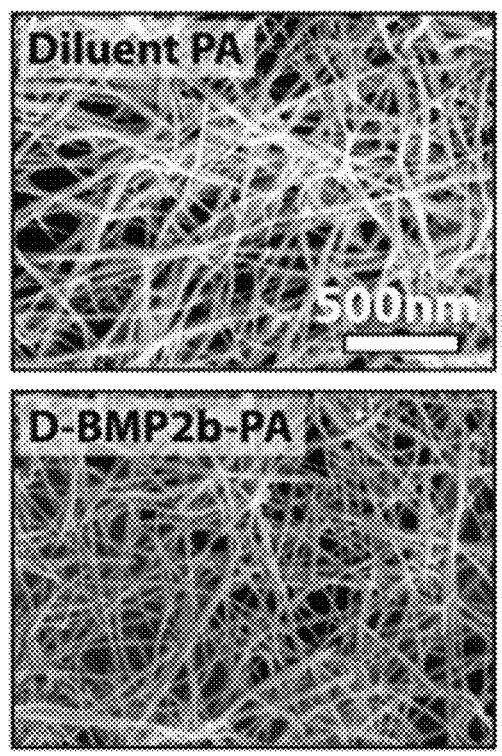
FIG. 10B

FIG. 10C
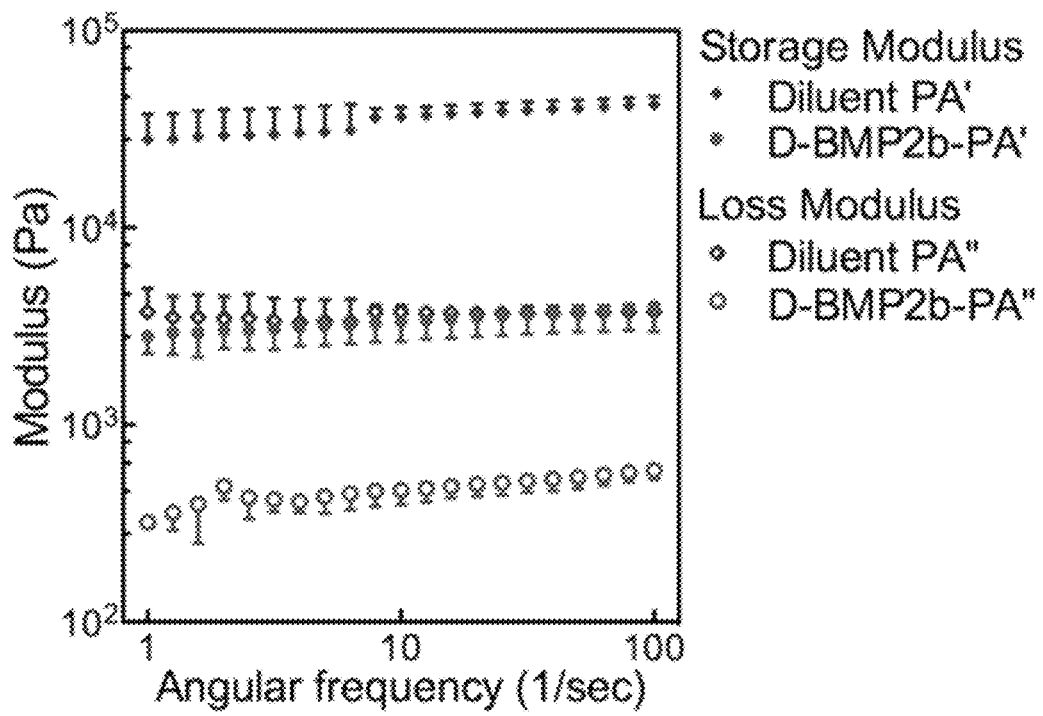
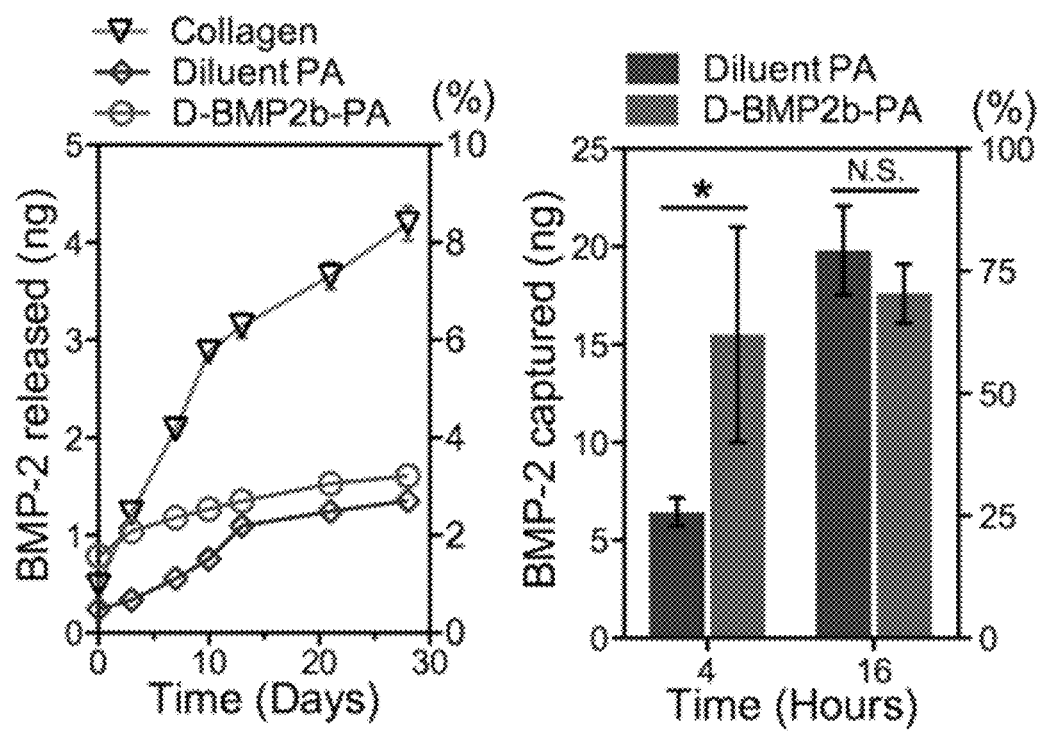
FIG. 10D
FIG. 10E

FIG. 12A
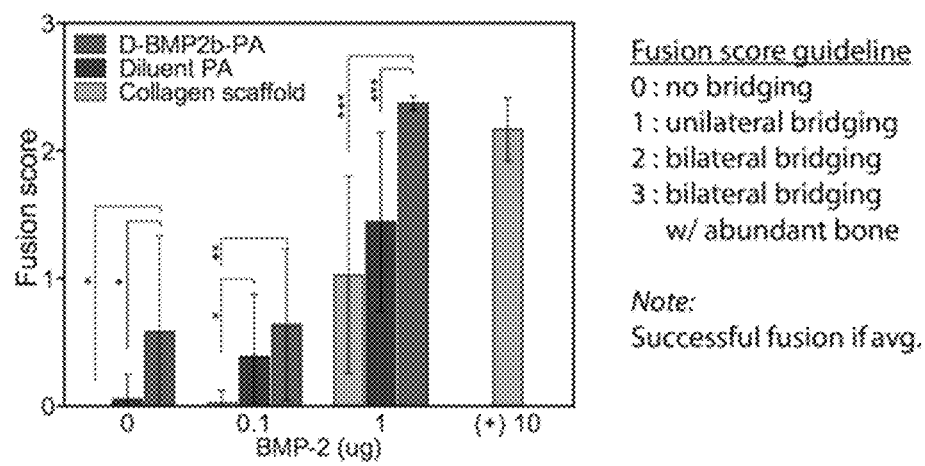
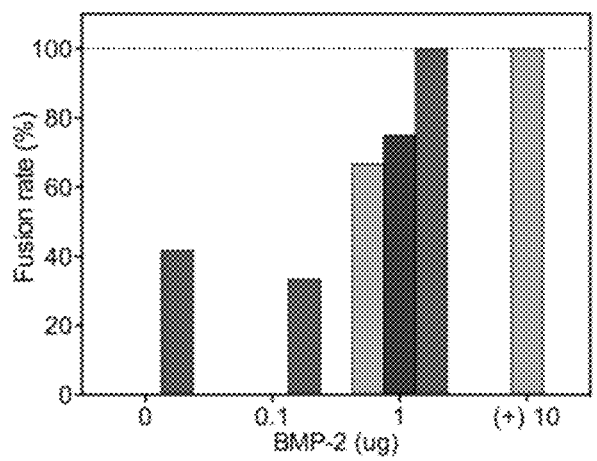
FIG. 12B
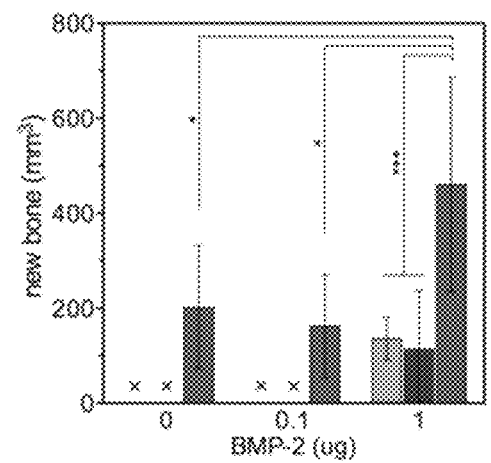
FIG. 12C

SEQUENCE LISTING

```
<160> NUMBER OF SEQ ID NOS: 12

<210> SEQ ID NO 1
<211> LENGTH: 11
<212> TYPE: PRT
<213> ORGANISM: Artificial sequence
<220> FEATURE:
<223> OTHER INFORMATION: BMP-2 binding peptide

<400> SEQUENCE: 1

Thr Ser Pro His Val Pro Tyr Gly Gly Gly Ser
1               5                   10

<210> SEQ ID NO 2
<211> LENGTH: 4
<212> TYPE: PRT
<213> ORGANISM: Artificial sequence
<220> FEATURE:
<223> OTHER INFORMATION: beta sheet forming segment

<400> SEQUENCE: 2

Ala Ala Val Val
1

<210> SEQ ID NO 3
<211> LENGTH: 6
<212> TYPE: PRT
<213> ORGANISM: Artificial sequence
<220> FEATURE:
<223> OTHER INFORMATION: beta sheet forming segment

<400> SEQUENCE: 3

Ala Ala Ala Val Val Val
1               5

<210> SEQ ID NO 4
<211> LENGTH: 11
<212> TYPE: PRT
<213> ORGANISM: Artificial sequence
<220> FEATURE:
<223> OTHER INFORMATION: Peptide amphiphile
<220> FEATURE:
<221> NAME/KEY: MISC_FEATURE
<222> LOCATION: (1)..(1)
<223> OTHER INFORMATION: C12-(K)V3A3E3 tail
<220> FEATURE:
<221> NAME/KEY: MISC_FEATURE
<222> LOCATION: (11)..(11)
<223> OTHER INFORMATION: NH2 tail

<400> SEQUENCE: 4

Ser Gly Gly Gly Tyr Pro Val His Pro Ser Thr
1               5                   10

<210> SEQ ID NO 5
<211> LENGTH: 26
<212> TYPE: DNA
<213> ORGANISM: Artificial sequence
```

<220> FEATURE:
<223> OTHER INFORMATION: DNA primer

<400> SEQUENCE: 5
atgcttcatt cattcgcctc acaaac					26

<210> SEQ ID NO 6
<211> LENGTH: 18
<212> TYPE: DNA
<213> ORGANISM: Artificial sequence
<220> FEATURE:
<223> OTHER INFORMATION: DNA Primer

<400> SEQUENCE: 6
ccaaaagaag ctttgctg					18

<210> SEQ ID NO 7
<211> LENGTH: 25
<212> TYPE: DNA
<213> ORGANISM: Artificial sequence
<220> FEATURE:
<223> OTHER INFORMATION: DNA Primer

<400> SEQUENCE: 7
ttaagcttgc gtcctctctg cttga					25

<210> SEQ ID NO 8
<211> LENGTH: 26
<212> TYPE: DNA
<213> ORGANISM: Artificial sequence
<220> FEATURE:
<223> OTHER INFORMATION: DNA Primer

<400> SEQUENCE: 8
tttctagatc agatctctag caggtt					26

<210> SEQ ID NO 9
<211> LENGTH: 20
<212> TYPE: DNA
<213> ORGANISM: Artificial sequence
<220> FEATURE:
<223> OTHER INFORMATION: DNA Primer

<400> SEQUENCE: 9
caagtcccac acagcagctt					20

<210> SEQ ID NO 10
<211> LENGTH: 20
<212> TYPE: DNA
<213> ORGANISM: Artificial sequence
<220> FEATURE:
<223> OTHER INFORMATION: DNA Primer

<400> SEQUENCE: 10
aaagccgagc tgccagagtt					20

<210> SEQ ID NO 11
<211> LENGTH: 25
<212> TYPE: DNA
<213> ORGANISM: Artificial sequence
<220> FEATURE:
<223> OTHER INFORMATION: DNA Primer

<400> SEQUENCE: 11
tgaaggtcgg tgtgaacgga ttggc					25

```
<210> SEQ ID NO 12
<211> LENGTH: 24
<212> TYPE: DNA
<213> ORGANISM: Artificial sequence
<220> FEATURE:
<223> OTHER INFORMATION: DNA Primer

<400> SEQUENCE: 12
catgtaggcc atgaggtcca ccac                                          24
```

BMP-2-BINDING PEPTIDE AMPHIPHILE NANOFIBERS

CROSS-REFERENCE TO RELATED APPLICATIONS

The present invention is a continuation of U.S. patent application Ser. No. 14/963,847, filed Dec. 9, 2015, which claims the priority benefit of U.S. Provisional Patent Application 62/089,560, filed Dec. 9, 2014, each of which is incorporated by reference in its entirety.

STATEMENT REGARDING FEDERALLY SPONSORED RESEARCH OR DEVELOPMENT

This invention was made with government support under W911NF-09-1-0044 awarded by the Army Research Office Subcontract to Northwestern University from University of Texas Subaward Number 0006726(C) and R01 DE015920 awarded by the National Institutes of Health. The government has certain rights in the invention.

FIELD

Provided herein are peptide amphiphiles with binding affinity for the bone promoting growth factor BMP-2, and methods of use thereof. In particular nanofibers and gel scoffolds of BMP-2-binding peptide amphiphiles are provided.

BACKGROUND

Pseudarthrosis—the non-union of bone in fractures, therapeutic bone fusions, or skeletal defects—remains a significant clinical challenge despite recent advances on implantable medical devices and use of biologics such as growth factors. In the United States alone, current estimates suggest that over 200,000 spine fusion procedures are performed annually with pseudarthrosis reported to be as high as 10-15% overall and as high as 48% in posterolateral intertransverse process lumbar fusions (Hsu et al. Global Spine J 2012, 02, 239; Aghdasi et al. Surgeon 2013, 11, 39; incorporated by reference in their entireties). In addition, approximately 6 million bone fractures are reported to occur annually with 10% resulting in delayed or impaired healing (Latham & Lau, Techniques in Orthopaedics 2011, 26, 14; Aghdasi et al. Surgeon 2013, 11, 39; incorporated by reference in their entireties). With increasing average life expectancy, the burden of musculoskeletal disease will become more prominent, and thus there is a great demand for improved treatment methods to maintain quality of life.

Recombinant human bone morphogenetic protein-2 (BMP-2) in combination with an absorbable type I collagen sponge is a bone graft substitute widely used in challenging healing environments such as osteoporosis, nonunion repair, and multilevel fusions. As a critical growth factor that greatly influences the osteoinductivity of bone grafts, BMP-2 delivered on a collagen sponge has demonstrated highly enhanced bone formation in long bone defect repairs and spinal arthrodesis (Reddi, Nature Biotechnology 1998, 16, 247; incorporated by reference in its entirety). However, efficient healing requires supraphysiologic doses of the cytokine, which may lead to surgical complications including bone resorption, graft migration, hematoma formation, radiculitis, and heterotopic ossification (Brower & Vickroy, Spine 2008, 33, E653; Muchow et al. Spine J 2010, 10, el.; Vaidya et al. J Spinal Disord Tech 2008, 21, 557; Wong et al. The Spine Journal 2008, 8, 1011; Aro et al. J Bone Joint Surg Am 2011, 93, 801; incorporated by reference in their entireties). The challenges associated with the current use of BMP-2 have lead to an extensive search for more optimal scaffolds that can reduce the therapeutic dose of the cytokine and thus lower the potential risks (Willie et al. Soft Matter 2010; Hsu et al. Spine 2013, 38, E691; incorporated by reference in their entireties). One proven approach is the development of biomaterials that can release one or more growth factors with controlled kinetics (Lee et al. Soc Interface 2011, 8, 153; Shah et al. Sci Transl Med 2013, 5, 191ra83; Benoit et al. Adv Funct Mater 2007, 17, 2085; incorporated by reference in their entireties). In addition, recent efforts have been made to develop biomimetic materials that not only better retain the therapeutic agent, but also provide an artificial extracellular environment that mimics the endogenous healing process, thereby maximizing the bioactivity of the therapeutic (Lutolf et al. Nature 2009, 462, 433; Pashuck et al. Sci Transl Med 2012, 4, 160sr4; Hudalla & Murphy, Adv Funct Mater 2011, 21, 1754; incorporated by reference in their entireties).

Peptide amphiphile (PA) molecules have been demonstrated to be useful as building blocks to create biomaterials for regenerative medicine. These PAs are designed to self-assemble in aqueous conditions into high-aspect-ratio nanofibers that are biomimetic of extracellular filaments measuring approximately 10 nanometers in diameter and microns in length. Their formation is driven mainly by secondary interactions such as collapse of hydrophobic molecular segments away from an aqueous environment and hydrogen bonding among peptide segments leading to β-sheet secondary structure (Hartgerink, E. Beniash, S. Stupp, Science 2001, 294, 1684; incorporated by reference in their entireties). These supramolecular nanofibers are programmed to display a high surface density of biological cues and this way function as artificial extracellular matrices (ECM) for regenerative medicine (Matson, R. H. Zha, S. I. Stupp, Current Opinion in Solid State and Materials Science 2011, 15, 225; incorporated by reference in their entireties). Previous examples include repair of the central nervous system and cartilage, neovascularization of ischemic heart tissue, enamel growth, and bone repair, among others (Tysseling-Mattiace et al. Journal of Neuroscience 2008, 28, 3814; Shah et al. Proceedings of the National Academy of Sciences 2010, 107, 3293; Webber et al. Proceedings of the National Academy of Sciences 2011, 108, 13438; Huang et al. Biomaterials 2010, 31, 9202; Mata et al. Biomaterials 2010, 31, 6004; Sargeant et al/Biomaterials 2008, 29, 161; incorporated by reference in their entireties).

PAs have also been developed to create therapeutic gels with prolonged release of growth factors (Rajangam et al. Nano letters 2006, 6, 2086; Lee et al. Biomaterials 2012, 34, 452; incorporated by reference in their entireties). It has been shown that heparan sulfate-like glycosaminoglycans (HSGAGs), which are rich in sulfo- and carboxyl-groups, bind and localize growth factors and enhance their signaling by facilitating ligand-receptor interactions[28,29]. Our laboratory previously designed a PA bearing a Cardin-Weintraub heparin-binding domain such that nanofibers formed by this molecule would bind HSGAGs, creating a biomimetic matrix. This heparin-binding PA (HBPA) gel exhibited substantial neo-vascularization in a rat cornea angiogenesis model using only nanogram quantities of angiogenic growth factors (Rajangam et al. Biomaterials 2008, 29, 3298; incorporated by reference in its entirety). Interestingly, the HBPA-polysaccharide gel without exogenous growth factors was sufficient to promote the formation of new vasculature in a mouse dorsal skinfold chamber model (Ghanaati et al. Biomaterials 2009, 30, 6062; incorporated by reference in its entirety). Furthermore, the HBPA system exhibited enhanced bone regeneration with a high probability of bridging in a rat critical-size femur defect model using only 1 µg BMP-2, a dose that is less than one tenth of the required dose for union in that model (Lee, B. J. Huang, S. R. Kaltz, S. Sur, C. J. Newcomb, S. R. Stock, R. N. Shah, S. I. Stupp, Biomaterials 2012, 34, 452; incorporated by reference in its entirety). In a separate study, a PA was designed with a binding segment to transforming growth factor β-1 (TGFβ-1) with the aim of creating a nanofiber matrix that could localize and recruit endogenous cytokine (Shah, N. A. Shah, M. M. Del Rosario Lim, C. Hsieh, G. Nuber, S. I. Stupp, Proceedings of the National Academy of Sciences 2010, 107, 3293; incorporated by reference in its entirety). The supramolecular gel prepared by co-assembling this bioactive PA with a diluent PA that lacks the binding sequence promoted regeneration of articular cartilage in a rabbit chondral defect microfracture model even without the addition of exogenous TGFβ-1.

SUMMARY

Provided herein are peptide amphiphiles with binding affinity for the bone promoting growth factor BMP-2, and methods of use thereof. In particular nanofibers and gel scoffolds of BMP-2-binding peptide amphiphiles are provided.

In some embodiments, the peptide amphiphile comprises: (a) a hydrophobic non-peptidic segment; (b) a β-sheet-forming peptide segment; (c) an acidic peptide segment; and (d) a BMP-2 binding peptide; wherein the hydrophobic non-peptidic segment is covalently attached to the N-terminus of the β-sheet-forming peptide segment; wherein the C-terminus of the β-sheet-forming peptide segment is covalently attached to the N-terminus of the acidic peptide segment; and wherein the C-terminus of the acidic peptide segment is covalently attached to the N-terminus of the BMP-2 binding peptide. In some embodiments, the hydrophobic non-peptidic segment comprises an acyl chain. In some embodiments, the acyl chain comprises $C_6$-$C_{20}$. In some embodiments, the acyl chain comprises lauric acid. In some embodiments, the β-sheet-forming peptide segment comprises AAAVVV (SEQ ID NO:3). In some embodiments, the acid peptide segment comprises a Glu (E) and/or Asp (D) residues. In some embodiments, wherein the acidic peptide segment comprises 2-7 amino acids in length with 50% or more amino acids selected from Glu (E) and/or Asp (D) residues. In some embodiments, the acidic peptide segment comprises EEE. In some embodiments, the binding sequence comprises a 6 amino acid segment with at least 50% sequence identity with TSPHVPYGGGS (SEQ ID NO:1). In some embodiments, the binding sequence comprises TSPHVPYGGGS (SEQ ID NO:1).

In some embodiments, provided herein are self-assembled nanofibers comprising: (a) a first plurality of peptide amphiphiles comprising: (i) a hydrophobic non-peptidic segment; (ii) a β-sheet-forming peptide segment; (iii) an acidic peptide segment; and (iv) a BMP-2 binding peptide; wherein the hydrophobic non-peptidic segment is covalently attached to the N-terminus of the β-sheet-forming peptide segment; wherein the C-terminus of the β-sheet-forming peptide segment is covalently attached to the N-terminus of the acidic peptide segment; and wherein the C-terminus of the acidic peptide segment is covalently attached to the N-terminus of the BMP-2 binding peptide; and (b) a second plurality of peptide amphiphiles comprising: (i) a hydrophobic non-peptidic segment; (ii) a β-sheet-forming peptide segment; and (iii) an acidic peptide segment; wherein the hydrophobic non-peptidic segment is covalently attached to the N-terminus of the β-sheet-forming peptide segment; wherein the C-terminus of the β-sheet-forming peptide segment is covalently attached to the N-terminus of the acidic peptide segment In some embodiments, the first plurality of peptide amphiphiles and the second plurality of peptide amphiphiles comprise the same a hydrophobic non-peptidic segments, β-sheet-forming peptide segments, and acidic peptide segments. In some embodiments, the peptide amphiphiles of the second plurality of peptide amphiphiles do not comprise a BMP-2 binding peptide, and the acidic peptide is the N-terminus of the peptide amphiphiles. In some embodiments, the first plurality of peptide amphiphiles and the second plurality of peptide amphiphiles are present at a ratio between 1:10 and 10:1 (e.g., 1:2, 2:1, etc.).

In some embodiments, provided herein are gel scaffolds comprising the self-assembled nanofibers described herein.

In some embodiments, provided herein are methods of promoting osteogenesis comprising administering to a subject the peptide amphiphiles, self-assembled nanofibers, and/or gel scaffolds described herein.

In some embodiments, provided herein are methods of promoting arthrodesis comprising administering to a subject the peptide amphiphiles, self-assembled nanofibers, and/or gel scaffolds described herein.

In some embodiments, provided herein are methods of promoting spinal fusion comprising administering to a subject the peptide amphiphiles, self-assembled nanofibers, and/or gel scaffolds described herein.

BRIEF DESCRIPTION OF THE DRAWINGS

FIGS. 1B-D are exploded views of the chemical structure. (E) Circular dichroism for the BMP-2-binding PA and the diluent PA demonstrating β-sheet secondary structures. (F) Cryogenic transmission electron microscopy (Cryo-TEM) showing the filamentous nanostructures of the diluent PA, the BMP-2-binding PA, and the diluted BMP-2-binding PA.

FIGS. 10A-E. Characterization of PA nanofiber gels. (A) Photograph of self-supporting PA gels. (B) Scanning electron microscopy (SEM) showing a network of filamentous nanostructures in the PA gels. (C) Rheological values of the diluted BMP-2-binding PA gel and the diluent PA gel at 1 wt % final concentration. Gels were equilibrated for 30 min at 37° C. prior to measurement. (D) In vitro analysis of BMP-2 release from the diluted BMP-2-binding PA gel and the diluent PA gel in comparison to a bare collagen scaffold over 28 days. (E) In vitro analysis of BMP-2 capture by the diluted BMP-2-binding PA gel and the diluent PA gel at 4 and 16 hours.

FIGS. 12A-D. BMP-2-binding PA gel promotes spinal arthrodesis in rats. Each animal received two identical graft materials with an equal dose of BMP-2 on both sides of the transverse processes. Graft materials consisted of the diluted BMP-2-binding PA gel, the diluent PA gel, or absorbable collagen sponge. The indicated dose of BMP-2 is the total per animal. (A) Fusion scores from blind manual palpation analysis at 8 weeks post-operation. (B) Fusion rates of each treatment based manual palpation scores, where an average score greater than or equal to 1.0 was considered solidly fused. (C) The successfully fused specimens were analyzed by microcomputed tomography (XT) to compare fusion mass volume ($mm^3$). All data in this study are means±SD; *$P<0.05$, $P<0.01$, *$P<0.001$. (D) Representative spine reconstructions from μCT are shown for the successfully fused specimens. Scale bars shown in images. White arrows indicate the presence of fusion mass in the transverse processes.

DEFINITIONS

Figures 1A, 1B, 1C, 1D:
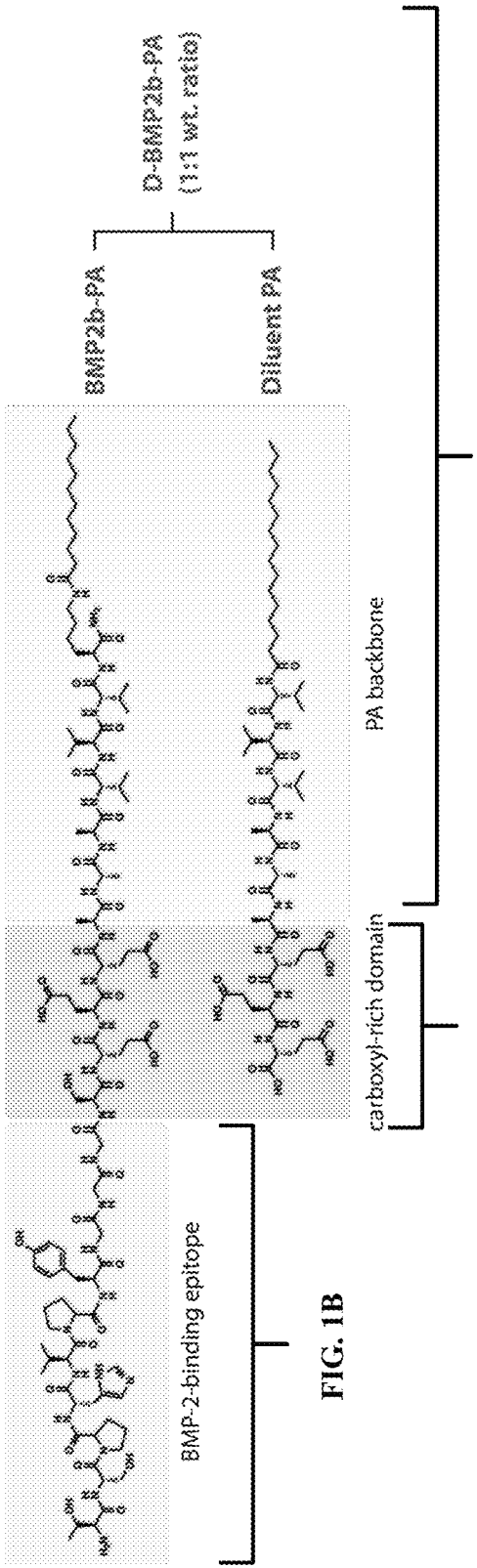
FIGS. 1A-F. Design and characterization of the BMP-2-binding PA nanofibers. (A-D) Chemical structures of the BMP-2-binding PA (BMP2b-PA) and the diluent PA, which will be mixed at equal wt. % ratio to form the diluted BMP-2-binding PA system (D-BMP2b-PA).
Figure 1B:
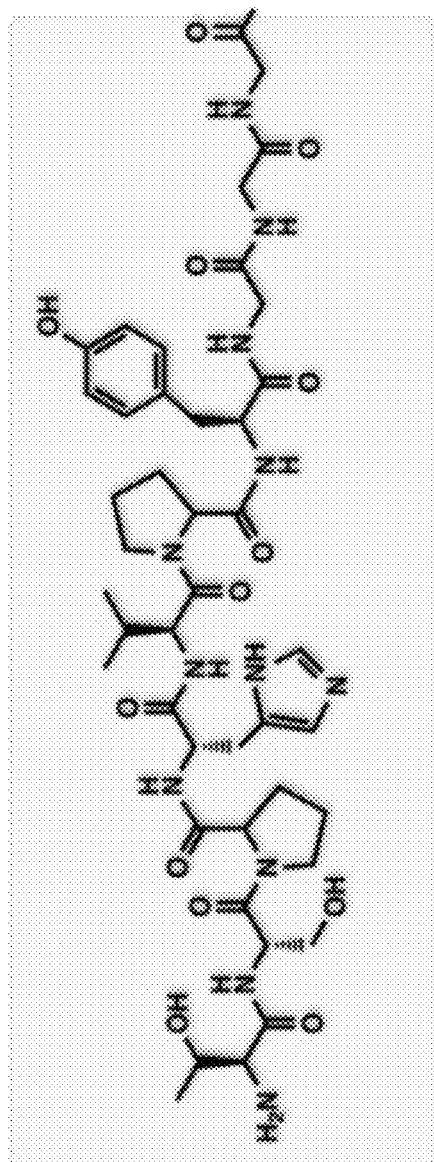
Figure 1C:
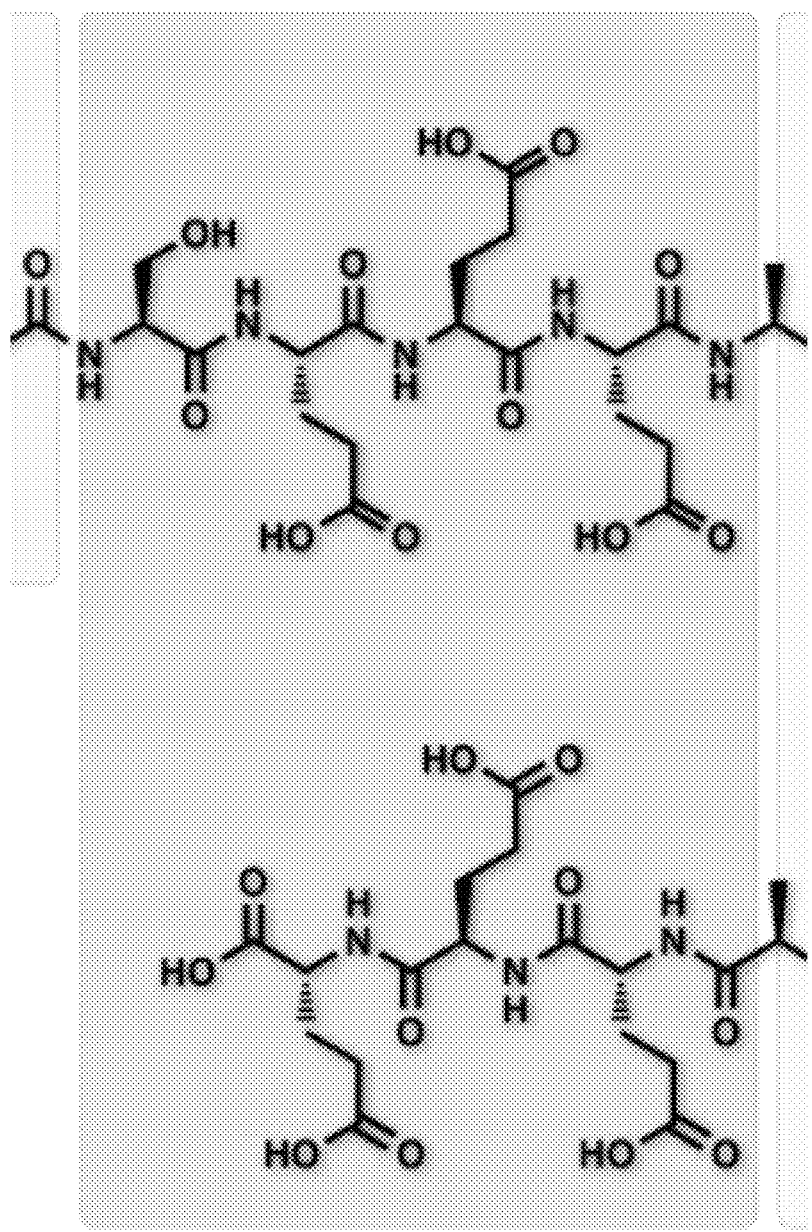
Figure 1D:
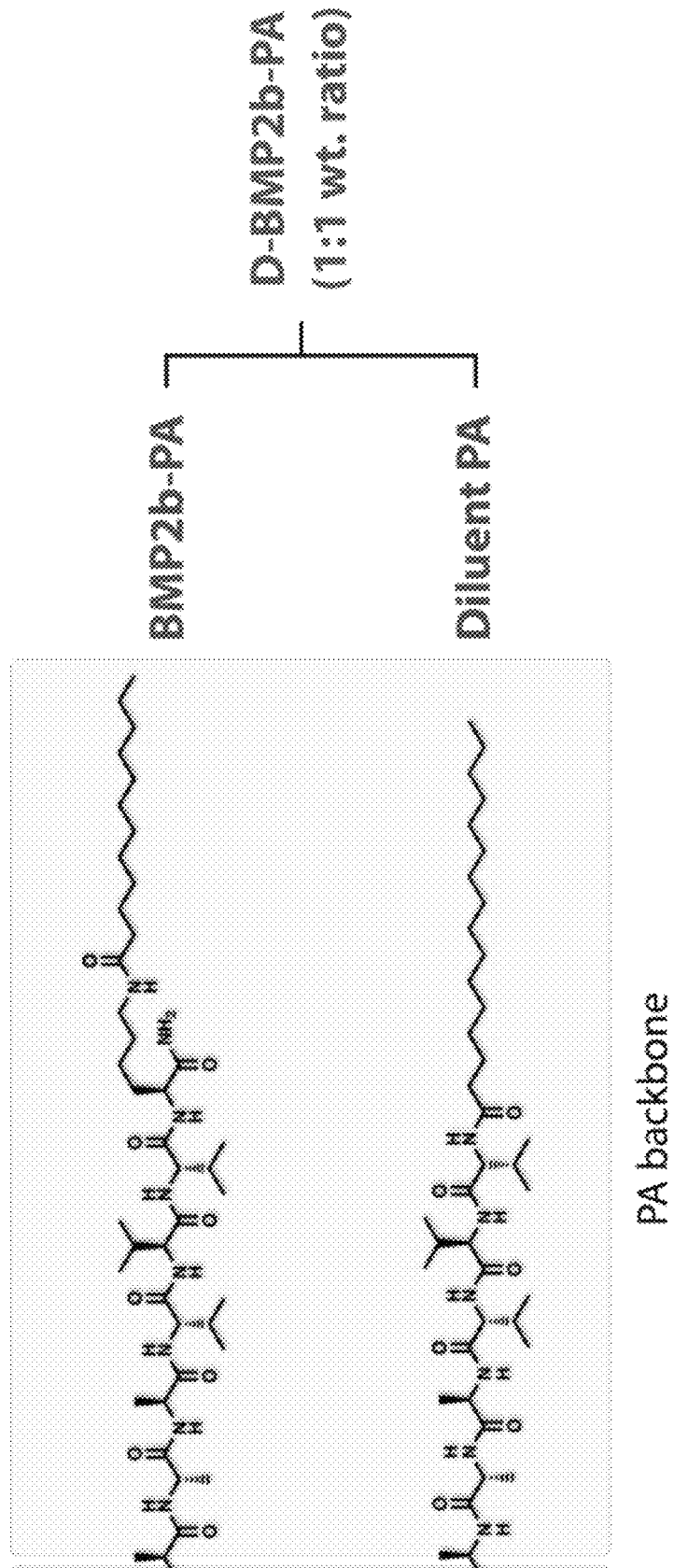
Figure 1E:
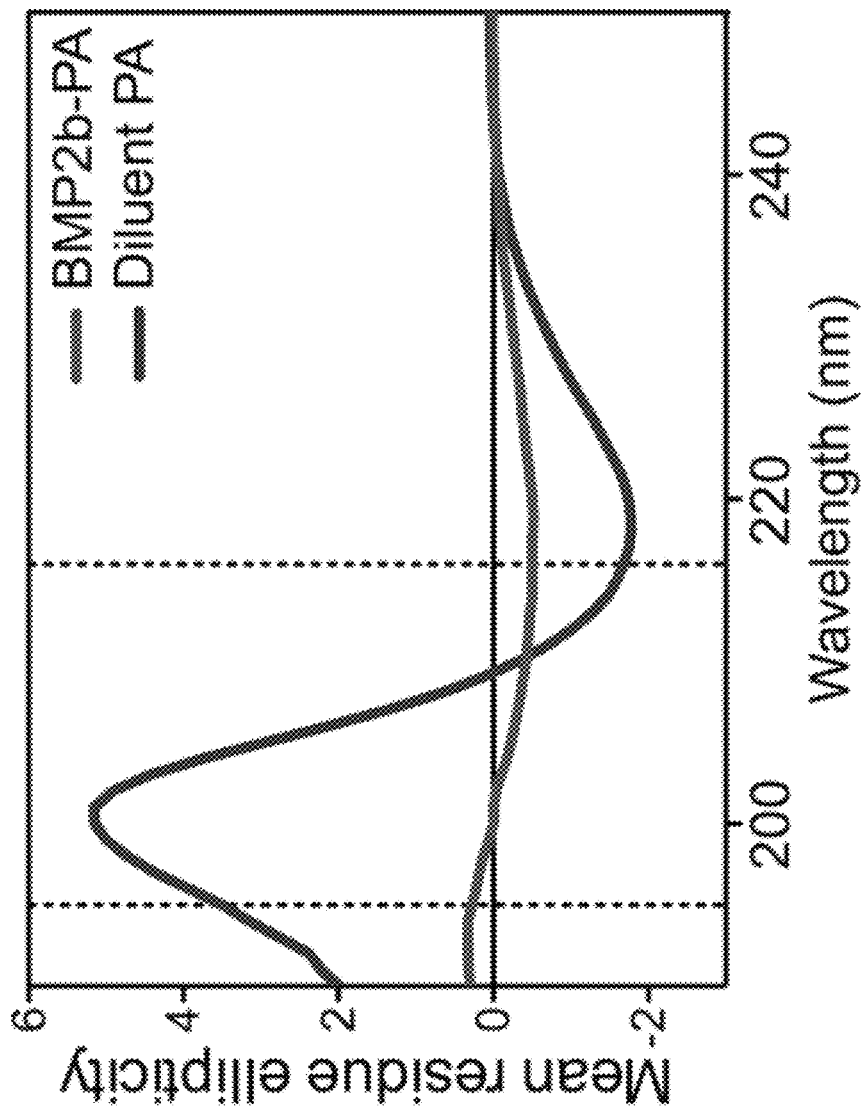
Figure 1F:
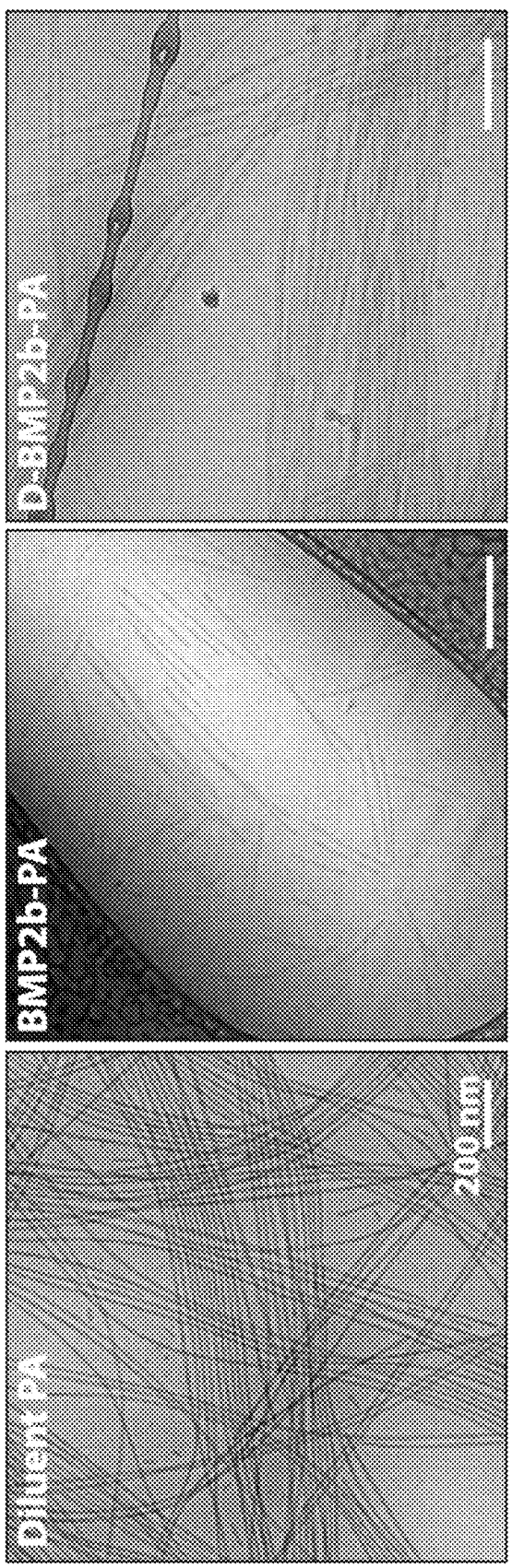
Figure 2A:
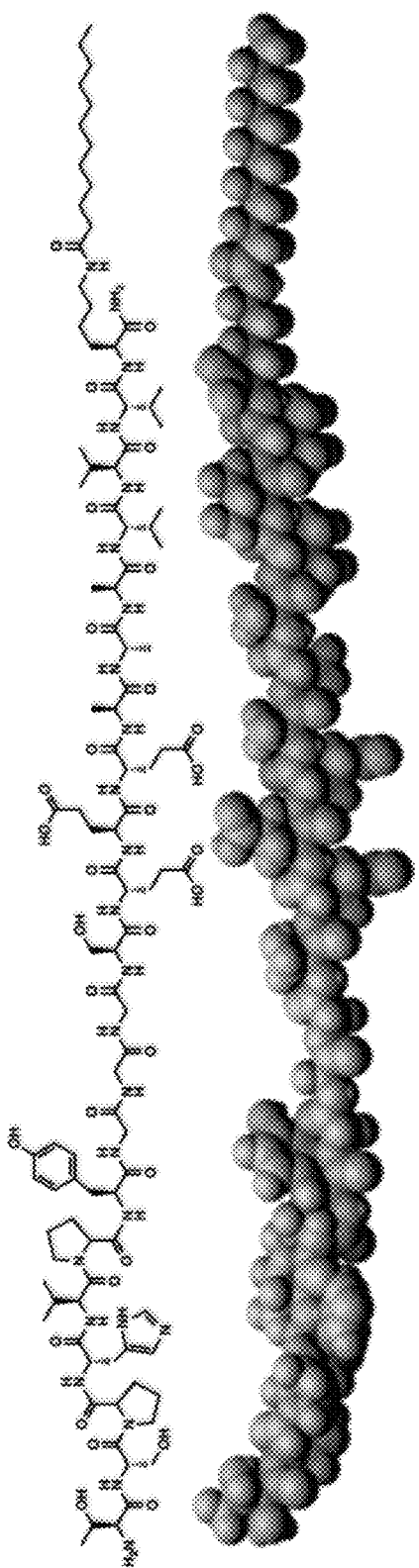
FIGS. 2A-E. Schematic representations of PA self-assembly. (A) The BMP-2-binding PA molecule. (B) The diluent PA molecule. (C) Representation of the diluent PA nanofiber assembly. (D) Representation of the BMP-2-binding PA nanofiber assembly. (E) Representation of the co-assembly between the BMP-2-binding PA and the diluent PA to form the diluted BMP-2-binding PA.
Figure 2B:
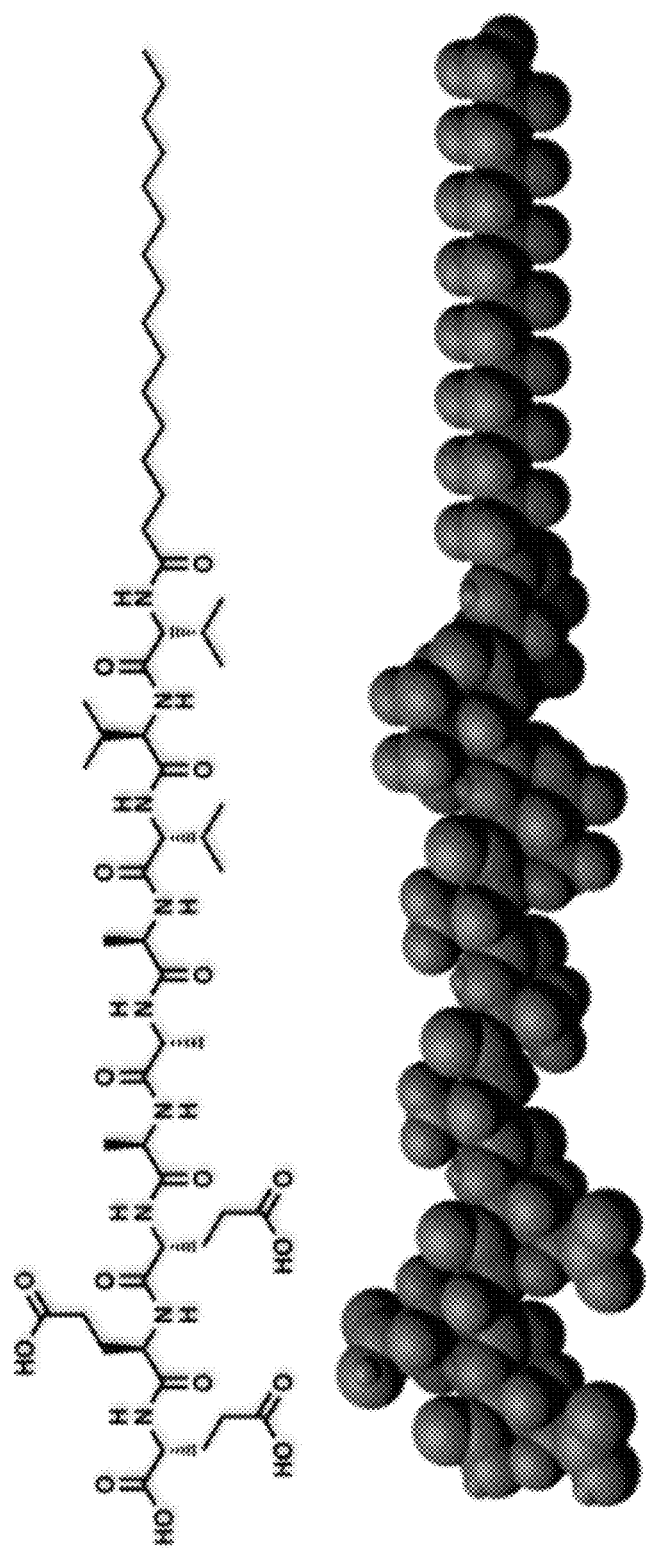
Figure 2C:
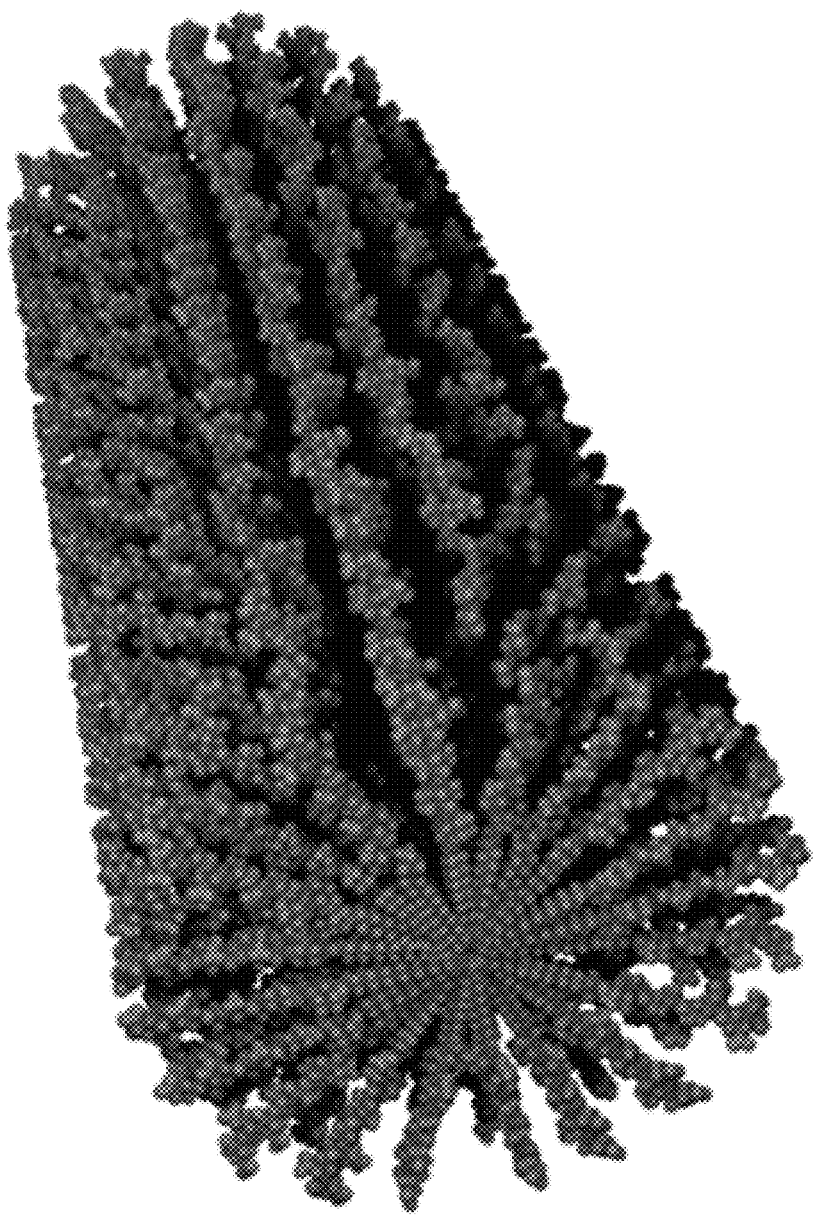
Figure 2D:
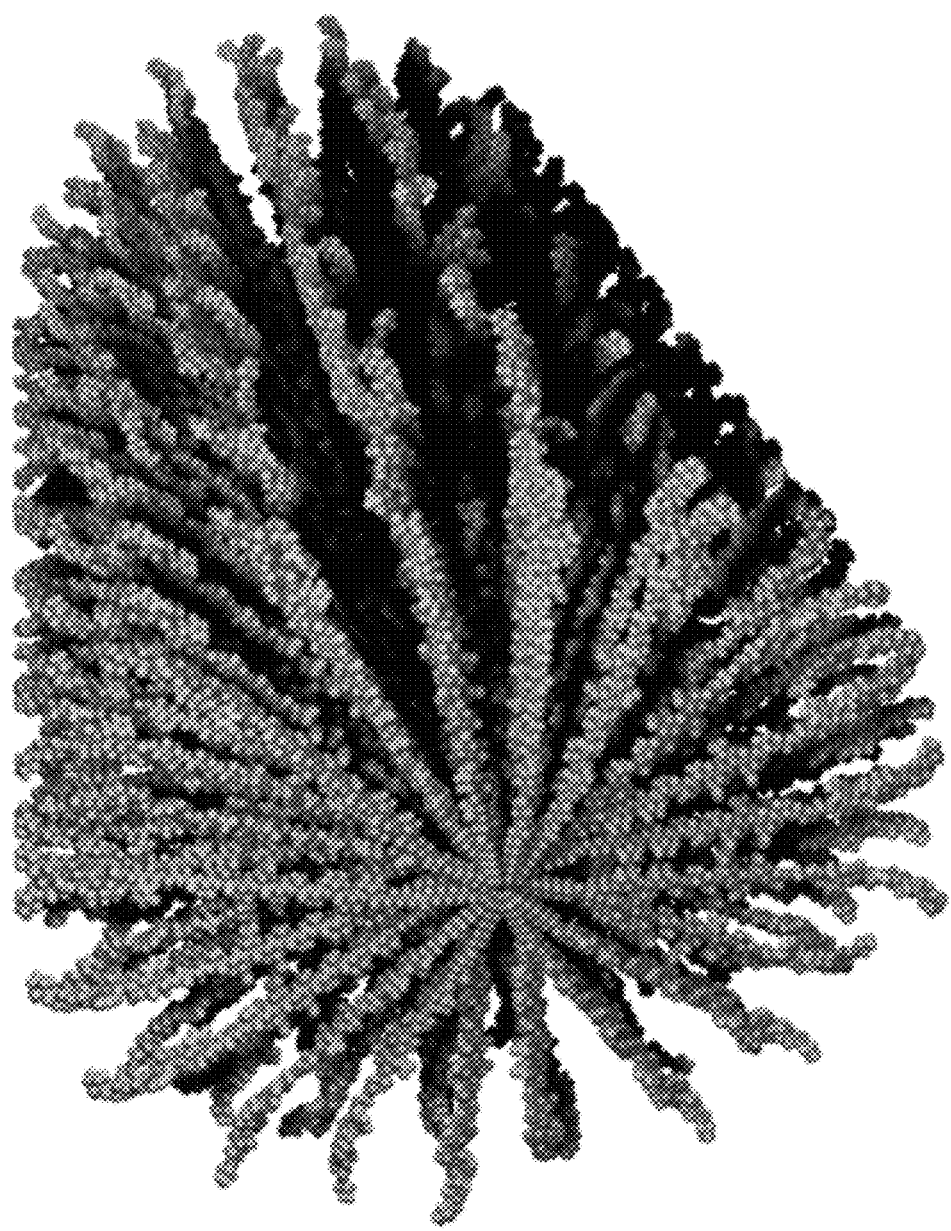
Figure 2E:
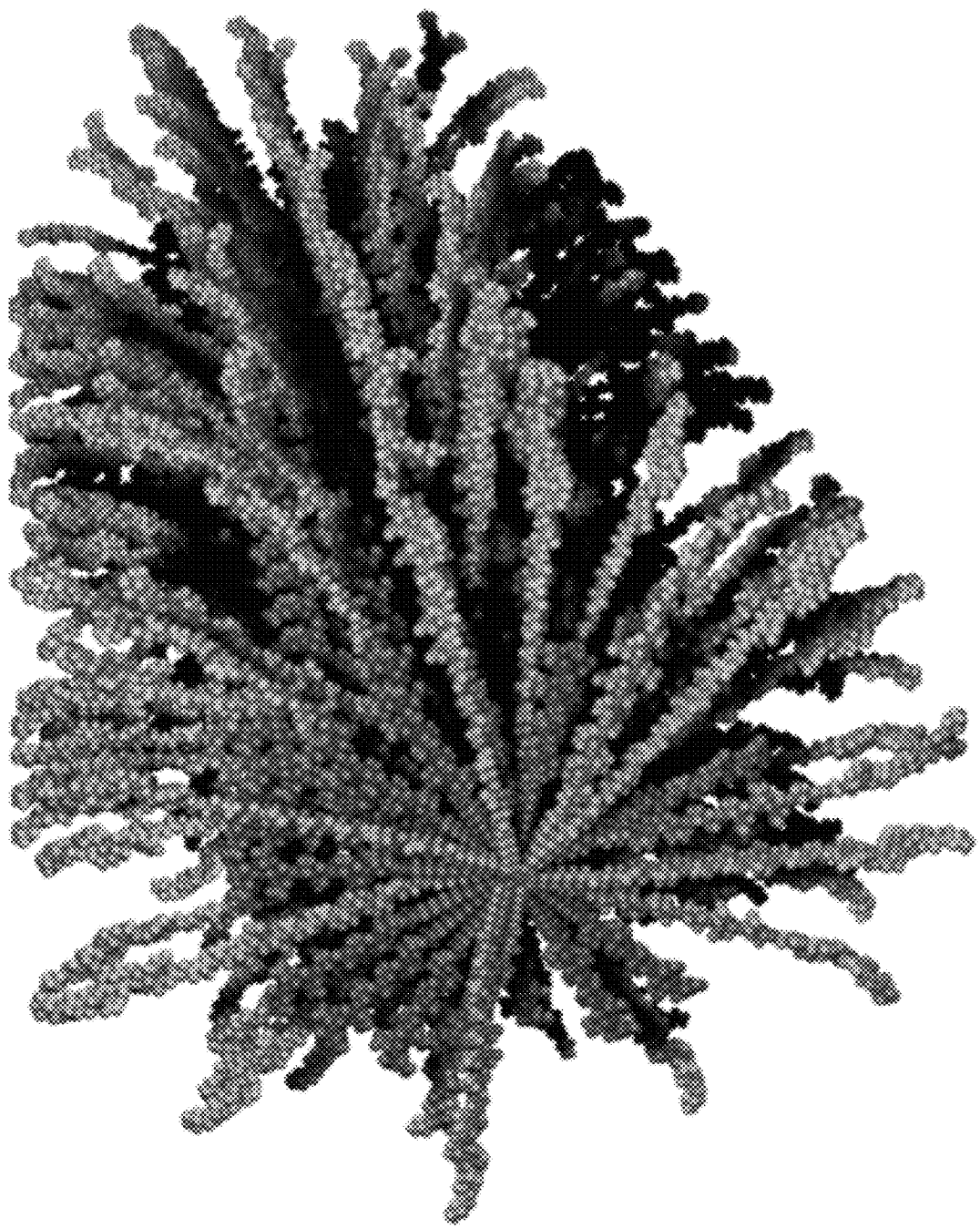

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a peptide amphiphile" is a reference to one or more peptide amphiphiles and equivalents thereof known to those skilled in the art, and so forth.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain functional group has been chemically blocked, reversibly or irreversibly, or otherwise modified to another functional group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term "peptide" refers a short polymer of amino acids linked together by peptide bonds. In contrast to other amino acid polymers (e.g., proteins, polypeptides, etc.), peptides are of about 50 amino acids or less in length. A peptide may comprise natural amino acids, non-natural amino acids, amino acid analogs, and/or modified amino acids. A peptide may be a subsequence of naturally occurring protein or a non-natural (artificial) sequence.

As used herein, the term "artificial" refers to compositions and systems that are designed or prepared by man, and are not naturally occurring. For example, an artificial peptide or nucleic acid is one comprising a non-natural sequence (e.g., a peptide without 100% identity with a naturally-occurring protein or a fragment thereof).

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Naturally occurring residues may be divided into classes based on common side chain properties, for example: polar positive (histidine (H), lysine (K), and arginine (R)); polar negative (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs.

Non-conservative substitutions may involve the exchange of a member of one class for a member from another class.

As used herein, the term "sequence identity" refers to the degree to which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

Any polypeptides described herein as having a particular percent sequence identity or similarity (e.g., at least 70%)

with a reference sequence ID number, may also be expressed as having a maximum number of substitutions (or terminal deletions) with respect to that reference sequence. For example, a sequence "having at least 70% sequence identity with SEQ ID NO:1" may have up to 3 substitutions relative to SEQ ID NO:1, and may therefore also be expressed as "having 3 or fewer substitutions relative to SEQ ID NO:1." Further, a sequence "having at least 80% sequence similarity with SEQ ID NO:1" may have 0, 1, or 2 non-conservative substitutions relative to SEQ ID NO:1, and may therefore also be expressed as "having 2 or fewer non-conservative substitutions relative to SEQ ID NO:1."

As used herein, the term "nanofiber" refers to an elongated or threadlike filament (e.g., having a significantly greater length dimension that width or diameter) with a diameter typically less than 100 nanometers.

As used herein, the term "supramolecular" (e.g., "supramolecular complex," "supramolecular interactions," "supramolecular fiber," "supramolecular polymer," etc.) refers to the non-covalent interactions between molecules (e.g., polymers, marcomolecules, etc.) and the multicomponent assemblies, complexes, systems, and/or fibers that form as a result.

As used herein, the term "physiological conditions" refers to the range of conditions of temperature, pH and tonicity (or osmolality) normally encountered within tissues in the body of a living human.

As used herein, the terms "self-assemble" and "self-assembly" refer to formation of a discrete, non-random, aggregate structure from component parts; said assembly occurring spontaneously through random movements of the components (e.g. molecules) due only to the inherent chemical or structural properties and attractive forces of those components.

As used herein, the term "peptide amphiphile" refers to a molecule that, at a minimum, includes a non-peptide lipophilic (hydrophobic) segment, a structural peptide segment and optionally a functional peptide segment. The peptide amphiphile may express a net charge at physiological pH, either a net positive or negative net charge, or may be zwitterionic (i.e., carrying both positive and negative charges). Certain peptide amphiphiles consist of or comprise: (1) a hydrophobic, non-peptidic segment (e.g., comprising an acyl group of six or more carbons), (2) a β-sheet-forming peptide segment; (3) a carboxyl-rich peptide segment, and (4) a functional moiety (e.g., BMP-2 binding moiety).

As used herein and in the appended claims, the term "lipophilic moiety" or "hydrophobic moiety" refers to the moiety disposed on the N-terminus of the peptide amphiphile (e.g., an acyl moiety), and may be herein and elsewhere referred to as the lipophilic or hydrophobic segment or component. The hydrophobic component should be of a sufficient length to provide amphiphilic behavior and micelle (or nanosphere or nanofiber) formation in water or another polar solvent system.

Accordingly, in the context of the embodiments described herein, the hydrophobic component preferably comprises a single, linear acyl chain of the formula: $C_{n-1}H_{2n-1}C(O)$— where n=6-22. In some embodiments, a linear acyl chain is the lipophilic group, palmitic acid. However, other small lipophilic groups may be used in place of the acyl chain.

As used herein, the term "structural peptide" or "beta-sheet forming peptide" refers to the intermediate amino acid sequence of the peptide amphiphile molecule between the hydrophobic segment and the charged peptide segment of the peptide amphiphile. This "structural peptide" or "beta-sheet forming peptide" is generally composed of three to ten amino acid residues with non-polar, uncharged side chains, selected for their propensity to form a beta-sheet secondary structure. Examples of suitable amino acid residues selected from the twenty naturally occurring amino acids include Met (M), Val (V), Ile (I), Cys (C), Tyr (Y), Phe (F), Gln (Q), Leu (L), Thr (T), Ala (A), and Gly (G) (listed in order of their propensity to form beta sheets). However, non-naturally occurring amino acids of similar beta-sheet forming propensity may also be used. Peptide segments capable of interacting to form beta sheets and/or with a propensity to form beta sheets are understood (See, e.g., Mayo et al. Protein Science (1996), 5:1301-1315; herein incorporated by reference in its entirety). In a preferred embodiment, the N-terminus of the structural peptide segment is covalently attached to the oxygen of the lipophilic segment and the C-terminus of the structural peptide segment is covalently attached to the N-terminus of the charged peptide segment.

As used herein, the terms "carboxy-rich peptide segment," "acidic peptide segment," and "negatively charged peptide segment" refer to the intermediately disposed peptide sequence between the structural peptide segment (beta-sheet forming segment) and the functional peptide (BMP-2 binding segment). In some embodiments, the carboxy-rich peptide segment two or more amino acid residues that have side chains displaying carboxylic acid side chains (e.g., Glu (E), Asp (D), or non-natural amino acides). A carboxy-rich peptide segment may optionally contain one or more additional (e.g., non-acidic) amino acid residues. Non-natural amino acid residues with acidic side chains could be used, as will be evident to one ordinarily skilled in the art. There may be from about 2 to about 7 amino acids, and or about 3 or 4 amino acids in this segment.

As used herein, the term "functional peptide" refers to amino acid sequences that mediate the action of sequences, molecules, or supramolecular complexes associated therewith. Peptide amphiphiles and structures (e.g., nanofibers) bearing functional peptides (e.g., BMP-2 binding peptides) exhibits the functionality of the functional peptide.

DETAILED DESCRIPTION

Provided herein are peptide amphiphiles with binding affinity for the bone promoting growth factor BMP-2, and methods of use thereof. In particular nanofibers and gel scaffolds of BMP-2-binding peptide amphiphiles are provided.

Provided herein is a self-assembling PA system that can bind both endogenous and exogenous BMP-2 (e.g., for use in bone regeneration). In some embodiments, the PA molecule design contains a carboxyl-rich peptide domain (E3) and a peptide segment with BMP-2-binding affinity, $NH_2$-TSPHVPYGGGS-COOH (SEQ ID NO:1), which was identified using phage display (Behanna, J. J. J. M. Donners, A. C. Gordon, S. I. Stupp, J Am Chem Soc 2005, 127, 1193; incorporated by reference in its entirety). This BMP-2-binding PA is evaluated co-assembled with negatively charged diluent molecules to space the BMP-2-binding segment. In vitro studies were performed to investigate the influence of this PA system and suitable controls on BMP-2-induced differentiation of C2C12 pre-myoblasts into an osteogenic lineage. Furthermore, the system's ability to promote osteogenesis in the clinically relevant procedure of spinal fusion was tested in vivo using a rat posterolateral lumbar intertransverse model.

Experiments conducted during development of embodiments described herein have demonstrated that self-assembling PA nanofibers with binding affinity for BMP-2 are effective in eliciting arthrodesis in a rat posterolateral lumbar intertransverse spinal fusion model. This BMP-2-binding PA system allowed a ten-fold reduction in the BMP-2 dose necessary to achieve 100% fusion rate, and also promoted a spinal fusion rate of 42% without exogenous BMP-2. It is contemplated that the observed efficacy in this translational model of bone regeneration is linked to the ability of the BMP2-binding nanofibers to potentiate osteogenesis signaling of both exogenously delivered and endogenously expressed growth factor; although, the present invention is not limited to any particular mechanism of action and an understanding of the mechanism of action is not necessary to practice the present invention. The bioactive nanofiber system provides approach to bone grafting for spine fusion without the undesirable side effects of high supraphysiologic doses of BMP-2.

Experiments conducted during development of embodiments described herein demonstrated the use of supramolecular nanofibers to promote osteogenesis in spinal fusion. The BMP-2-binding PA showed enhanced BMP-2-induced osteoblast differentiation in vitro, and when prepared as a gel it exhibited prolonged retention of the growth factor. Evaluation of this bioactive nanofiber gel in a rat posterolateral lumbar intertransverse spinal fusion model revealed a 100% fusion rate with increased bone formation when loaded with a BMP-2 dose ten-fold lower than that required for sufficient arthrodesis using a collagen sponge. Most importantly, a 42% spinal fusion rate was also achieved with the nanofiber gel alone without the addition of exogenous BMP-2. Overall, the efficacy demonstrated here supports the use of this PA system as a replacement for current clinical modes of BMP-2 use in the treatment of degenerative disc diseases and other spinal disorders.

Figure 9A:
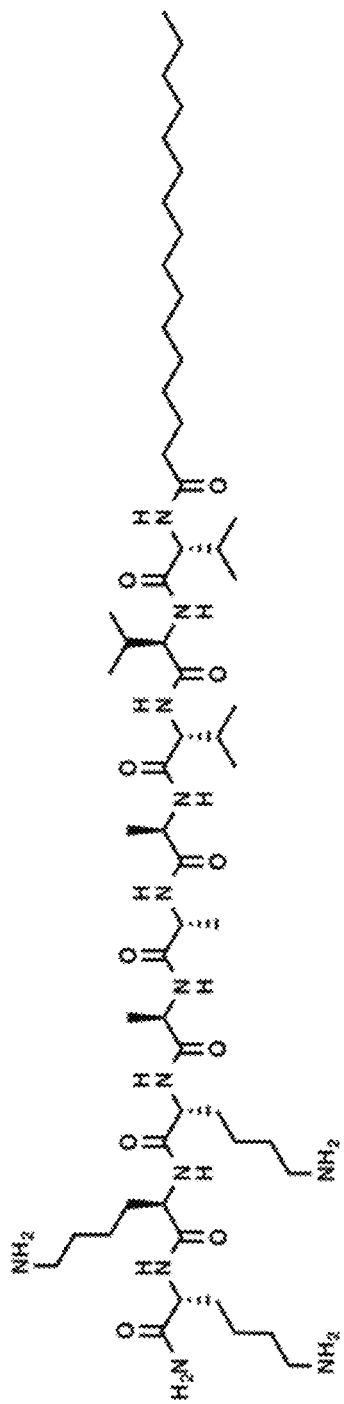
FIGS. 9A-B. (A) Chemical structures of the positively charged PA (K3 PA) which shares the same β-sheet forming sequence as the diluent PA. (B) C2C12 cells were seeded for 1 day prior to treatment with BMP-2 at 50 ng/mL and varying concentrations of the K3 PA. Alkaline phosphatase (ALP) enzyme activity was measured after 4 days, and measurements were normalized to their respective DNA content. The average values from each treatment are normalized to the BMP-2 control.
Figure 9B:
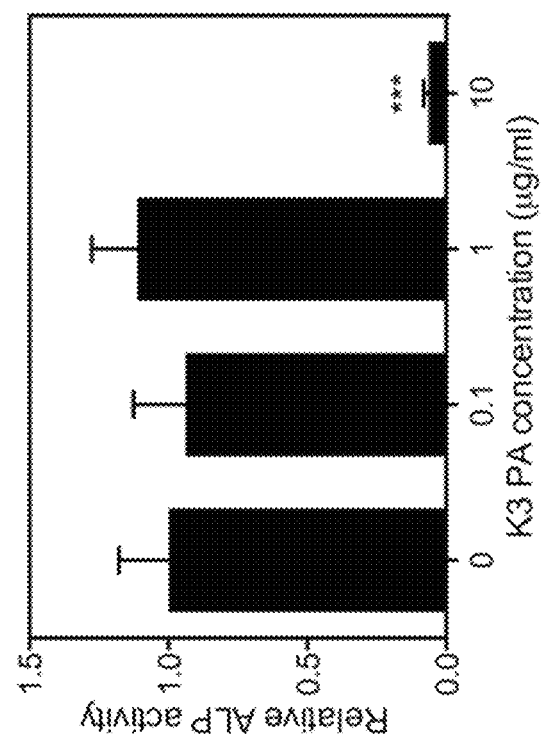

Heparan sulfate-like glycosaminoglycans (HSGAGs), rich in sulfo- and carboxyl-groups, are known to potentiate osteogenesis induced by BMP-2 in vitro and in vivo as well. Experiments conducted during development of embodiments described herein demonstrate that supramolecular nanofibers containing BMP-2-binding peptide sequences can mimic certain aspects of the natural polysaccharides and augment the BMP-2-induced osteoblast differentiation of C2C12 myoblasts in vitro. Results also revealed that negatively charged diluent PA nanofibers can also enhance the BMP-2-induced osteoblast differentiation as measured through the increased ALP activity and expression of other osteogenic gene markers. Since BMP-2 is a basic growth factor with an isoelectric point near 9.0, it is possible that the carboxyl residues on the nanofiber surface can bind BMP-2 by electrostatic attraction and exhibit heparin-like features which result in cell signaling. The importance of the electrostatic attraction between the basic protein and the acidic PA were verified by using a basic PA, which failed to enhance BMP-2-induced osteoblast differentiation of C2C12 cells (FIG. 9). Furthermore, when this diluent PA was co-assembled with the BMP-2-binding PA at 1:1 weight ratio, the resulting supramolecular nanofiber system exhibited greater enhancement of BMP-2 activity in comparison to either PA alone. It is contemplated that the dilution of the BMP-2-binding PA results in enhanced display of the binding sequences on the nanofiber surface, thus facilitating optimal binding interactions between the peptide sequence and BMP-2.

Similar to PA systems that have been investigated previously as therapeutic gels with controlled growth factor release, the diluted BMP-2-binding PA gel and the diluent PA gel showed BMP-2 release rates that were much slower than the burst release observed from the absorbable collagen sponge. In addition, there was no significant difference in the release profiles between the two PA nanofiber gels after 28 days at physiological pH; the diluent PA gel even exhibited better BMP-2 retention than the diluted BMP-2-binding PA gel during the first 10 days. This is in contrast to the SPR analysis, which showed that the BMP-2-binding PA had a greater binding affinity to BMP-2 than the diluent PA. However, due to the non-specific interactions between the PA nanofibers and the NTA-dextran substrate at pH 7.4, the SPR analysis was performed at pH 8.4 where there was minimal PA supramolecular assembly. Therefore, in the bulk PA gels, it is possible that the high charge density on the surface of the diluent PA nanofibers may elicit electrostatic binding to BMP-2 that was not captured by the SPR analysis. It has been previously observed that a gel made of the diluent PA nanofibers exhibited a very strong binding to several growth factors and this binding was diminished when the PA was co-assembled at 10 mol % level with a different PA which decreased its surface charge density. However, co-assembly of the diluent PA with the BMP2-binding PA did not provide the expected decrease in protein retention ability. This indicates that it is the BMP-2-binding epitope that is responsible for maintaining the same protein release profile even though the charge density has not been diminished. A difference between these two PA gels in their abilities to capture the growth factor from the medium was observed. After a 4 h incubation period, the diluted BMP-2-binding PA gel captured more BMP-2 than the diluent PA; however, BMP-2 captured by the two gels was comparable by 16 h. Since the BMP-2-binding PA exhibited a greater binding affinity to BMP-2 than the diluent PA in the SPR analysis, it is possible that the bioactive epitope is able to capture the growth factor faster during the early incubation period. However, the non-specific, electrostatic binding of BMP-2 by the diluent PA is accumulated over time, resulting in comparable amounts of BMP-2 captured by the two gels.

Effective spinal arthrodesis in the model utilized here is known to occur with the use of a collagen sponge containing 10 μg BMP-2. In contrast the diluted BMP-2-binding PA gel investigated here led to 100% fusion rate with a high probability of bilateral bridging using only 1 μg BMP-2, thus reducing the required growth factor dose by 10-fold. On the other hand, the diluent PA gel with the same growth factor dose (1 μg) elicited a fusion rate of 75%. The difference in fusion rates between these two nanofiber systems suggests that the therapeutic efficacy observed with the BMP-2-binding PA is not only due to a prolonged retention of the cytokine within the bulk gel, but also due in part to the inherent bioactivity of the nanofibers. It is contemplated that once mesenchymal stem cells make contact with or enter the PA gels, the presentation of BMP-2 by the BMP-2-binding nanofibers within the microenvironment potentiates protein signaling and promotes an enhanced osteogenesis.

Experiments conducted during development of embodiments described herein demonstrate a 42% spinal fusion rate with the use of the BMP-2-binding PA without any exogenous growth factor, whereas the diluent PA or collagen sponge did not show an innate ability to induce fusion. The average fusion mass volume by the bioactive PA was comparable to those treated with 1 μg BMP-2 incorporated in the diluent PA gel or the collagen sponge. These results indicate that the amount of endogenously expressed BMP-2 at the fusion bed site may be sufficient to promote osteogenesis in the presence of the bioactive nanofiber networks with specific protein-binding capacity. Similarly, heparan sulfate chains that are affinity-matched to BMP-2 have been reported to promote bone regeneration in a rabbit critical-size ulnar defect model by harnessing endogenously produced BMP-2.

In some embodiments, the peptide amphiphile molecules and compositions of the embodiments described herein are synthesized using preparatory techniques well-known to those skilled in the art, preferably, by standard solid-phase peptide synthesis, with the addition of a fatty acid in place of a standard amino acid at the N-terminus of the peptide, in order to create the lipophilic segment. Synthesis typically starts from the C-terminus, to which amino acids are sequentially added using either a Rink amide resin (resulting in an —NH$_2$ group at the C-terminus of the peptide after cleavage from the resin), or a Wang resin (resulting in an —OH group at the C-terminus). Accordingly, embodiments described herein encompasses peptide amphiphiles having a C-terminal moiety that may be selected from the group consisting of —H, —OH, —COOH, —CONH$_2$, and —NH$_2$.

The lipophilic segment is typically incorporated at the N-terminus of the peptide after the last amino acid coupling, and is composed of a fatty acid or other acid that is linked to the N-terminal amino acid through an acyl bond. In aqueous solutions, PA molecules self-assemble (e.g., into cylindrical micelles (a.k.a nanofibers)) that bury the lipophilic segment in their core and display the functional peptide on the surface. The structural peptide undergoes intermolecular hydrogen bonding to form beta sheets that orient parallel to the long axis of the micelle.

In some embodiments, compositions described herein comprise PA building blocks that in turn comprise a hydrophobic segment and a peptide segment. In certain embodiments, a hydrophobic (e.g., hydrocarbon and/or alkyl tail) segment of sufficient length (e.g., >3 carbons, >5 carbons, >7 carbons, >9 carbons, etc.) is covalently coupled to peptide segment (e.g., an ionic peptide having a preference for beta-strand conformations) to yield a peptide amphiphile molecule. In some embodiments, a plurality of such PAs will self-assemble in water (or aqueous solution) into a nanostrcuture (e.g., nanofiber). In various embodiments, the relative lengths of the peptide segment and hydrophobic segment result in differing PA molecular shape and nanostructural architecture. For example, a broader peptide segment and narrower hydrophobic segment results in a generally conical molecular shape that has an effect on the assembly of PAs (See, e.g., J. N. Israelachvili Intermolecular and surface forces; 2nd ed.; Academic: London San Diego, 1992; herein incorporated by reference in its entirety). Other molecular shapes have similar effects on assembly and nanostrcutural architecture. In various embodiments, hydrophobic segments pack in the center of the assembly with the peptide segments exposed to an aqueous or hydrophilic environment to form cylindrical nanostructures that resemble filaments. Such nanofilaments display the peptide regions on their exterior and have a hydrophobic core.

To induce self-assembly of an aqueous solution of peptide amphiphiles, the pH of the solution may be changed (raised or lowered) or multivalent ions, such as calcium, or charged polymers or other macromolecules may be added to the solution.

In some embodiments, the hydrophobic segment is a non-peptide segment (e.g., alkyl group). In some embodiments, the hydrophobic segment comprises an alkyl chain (e.g., saturated) of 4-25 carbons (e.g., 4, 5, 6, 7, 8, 9, 10, 11, 12, 13, 14, 15, 16, 17, 18, 19, 20, 21, 22, 23, 24, 25), fluorinated segments, fluorinated alkyl tails, aromatic segments, pi-conjugated segments, etc. In some embodiments, the hydrophobic segment comprises an acyl chain (e.g., saturated) of 4-25 carbons (e.g., 4, 5, 6, 7, 8, 9, 10, 11, 12, 13, 14, 15, 16, 17, 18, 19, 20, 21, 22, 23, 24, 25)

In some embodiments, peptide amphiphiles comprise a functional moiety. In particular embodiments, a functional moiety is the C-terminal most segment of the PA. In some embodiments, the functional moiety is attached to the C-terminal end of the charged segment. In some embodiments, the functional moiety is exposed on the surface of a assembled PA structure (e.g., nanofiber). A functional moiety is typically a peptide (e.g., BMP-2 binding peptide), but is not limited thereto. Examples described in detail herein utilize a peptide sequence that binds BMP-2 as a functional moiety. BMP-2 binding PA nanofibers result from such compositions. Functional peptides and other moieties for achieving such functionality will be understood.

In some embodiments, peptide amphiphiles and nanofibers described herein display a BMP-2 binding peptide (e.g., comprising TSPHVPYGGGS (SEQ ID NO:1), or functional analogues thereof). In some embodiments, a BMP-2 binding peptide comprises at least 50% sequence identity (e.g., 6, 7, 8, 9, 10, or 11 (or ranges there between) conserved positions) with SEQ ID NO:1. In some embodiments, a BMP-2 binding peptide comprises at least 70% sequence similarity (e.g., 3, 2, 1, or 0 (or ranges there between) non-conservative substitutions) with SEQ ID NO:1. In some embodiments, a BMP-2 binding peptide retains a substantial degree (e.g., 10%, 20%, 30%, 40%, 50%, 60%, 70%, 80%, 90%, 100%, or ranges there between) of the capacity of SEQ ID NO:1 to bind BMP-2. In some embodiments, a BMP-2 binding peptide has enhanced binding affinity for BMP-2 compared to SEQ ID NO:1 (e.g., 1.1-fold, 1.5-fold, 2-fold, 3-fold, 4-fold, 5-fold, 6-fold, 7-fold, 8-fold, 9-fold, 10-fold, or more, or ranges there between).

In some embodiments, peptide amphiphiles comprise an acidic peptide segment. For example, in some embodiments, the acidic peptide comprises two or more (e.g., 2, 3, 4, 5, 6, 7, or more) acidic residues (D or E) in sequence. In some embodiments, the acidic peptide segment comprises up to 7 residues in length and comprises at least 50% acidic residues.

In some embodiments, peptide amphiphiles comprise a beta sheet forming segment. In some embodiments, the beta sheet forming segment comprises an alanine- and valine-rich peptide segment (e.g., AAVV (SEQ ID NO:2), AAAVVV (SEQ ID NO:3), or other combinations of V and A residues, etc.). In some embodiments, the beta sheet peptide comprises 4 or more consecutive A and/or V residues, or conservative or semi-conservative substitutions thereto. In some embodiments, the beta-sheet forming peptide segment comprises 4 or more consecutive non-polar aliphatic residues (e.g., alanine (A), valine (V), leucine (L), isoleucine (I), methionine (M)). In some embodiments, the beta-sheet forming peptide segment comprises 4-16 amino acids in length and comprises 4 or more (e.g., 4, 5, 6, 7, 8, 9, 10, 11, 12, 13, 14, 15, 16, or ranges there between) non-polar aliphatic residues.

Suitable peptide amphiphiles, PA segments, PA nanostructures, and associated reagents and methods are described, for example in U.S. Pat. Nos. 8,512,693; 8,450,271; 8,138,140; 8,124,583; 8,114,835; 8,114,834; 8,080,262; 8,063,014; 7,851,445; 7,838,491; 7,745,708; 7,683,025; 7,554,021; 7,544,661; 7,534,761; 7,491,690; 7,452,679; 7,390,526; 7,371,719; 6,890,654; herein incorporated by reference in their entireties.

The characteristics (e.g., shape, rigidity, hydrophilicity, etc.) of a PA supramolecular structure depend upon the identity of the components of a peptide amphiphile (e.g., lipophilic segment, acidic segment, structural segment, functional segment, etc.). For example, nanofibers, nanospheres, intermediate shapes, and other supramolecular structures are achieved by adjusting the identity of the PA component parts.

EXPERIMENTAL

Example 1

Results

Design and Characterization of the BMP-2-Binding PA

An exemplary BMP-2-binding PA (BMP2b-PA) was designed to display a BMP-2-binding peptide sequence on the surface of the nanofibers (FIG. 1). Since phage-displayed peptides are linked via the C terminus, a carboxyl-rich $E_3$ domain and an $A_3V_3$ β-sheet-forming domain were attached, followed by a terminal lysine with a $C_{12}$ alkyl chain linked to the ε-amino group (FIG. 1A). This sequence promotes supramolecular self-assembly into cylindrical nanofibers. The diluent PA was designed without the bioactive segment and contains only the $E_3$ domain linked at the N terminus a $A_3V_3$ β-sheet-forming domain, followed by a $C_{16}$ alkyl chain (FIG. 1A). The alkyl lengths of the two PAs were selected to match the length of the hydrophobic moieties of these two molecules. Repeated units of valines and alanines found in the BMP-2-binding PA and the diluent PA have been shown to promote self-assembly of other PA molecules into nanofibers via β-sheet formation along the length of the fibers (Pashuck, H. Cui, S. I. Stupp, J Am Chem Soc 2010, 132, 6041; herein incorporated by reference in its entirety). Circular dichroism (CD) studies verified that both PAs exhibited spectra that are indicative of β-sheets with a maximum near 195 nm and a minimum near 216 nm (FIG. 1E). The β-sheet signature of the diluent PA was red-shifted, a feature associated with twisting of the secondary structure. The BMP-2-binding PA and the diluent PA were co-assembled in aqueous conditions to form the diluted BMP-2-binding PA (D-BMP2b-PA), which was contemplated to display the binding segment on the nanofiber surface with higher accessibility to the protein than the BMP-2-binding PA alone (FIG. 2). Cryogenic transmission electron microscopy (cryo-TEM) revealed the formation of self-assembled cylindrical nanofibers for the diluent PA, BMP-2-binding PA, and the diluted BMP-2-binding PA (FIG. 1F). The diluent PA formed high-aspect-ratio nanofibers measuring microns in length, whereas the BMP-2-binding PA formed nanofibers with submicron lengths. When these two PAs were co-assembled at 1:1 weight ratio, high-aspect-ratio cylindrical nanofibers were observed.

Figure 3:
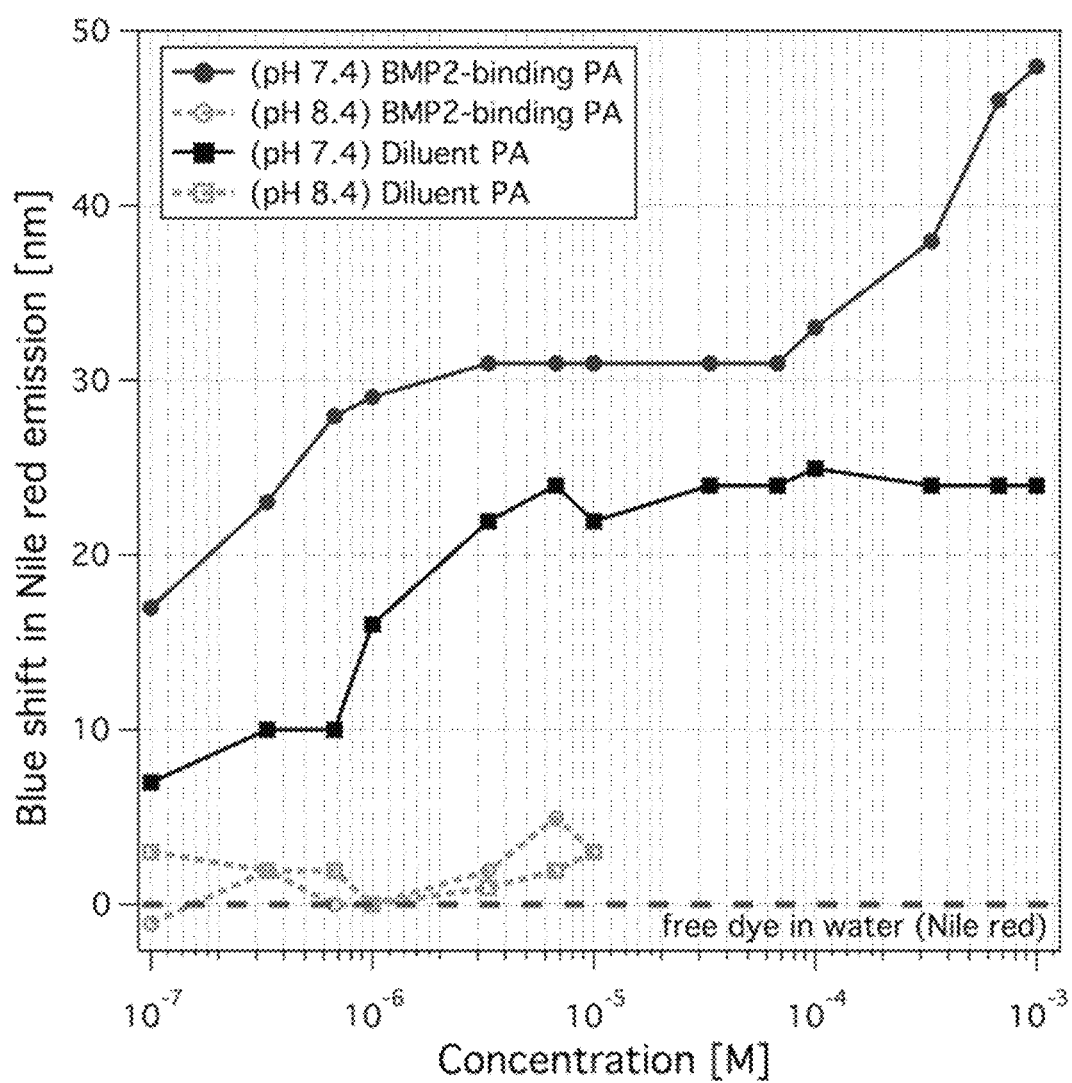
FIG. 3. Critical micelle concentration (CMC) analysis of the BMP-2-binding PA and the diluent PA at pH 7.4 and 8.4. Each solution contained the Nile red dye at 100 nM.
Figure 4A:
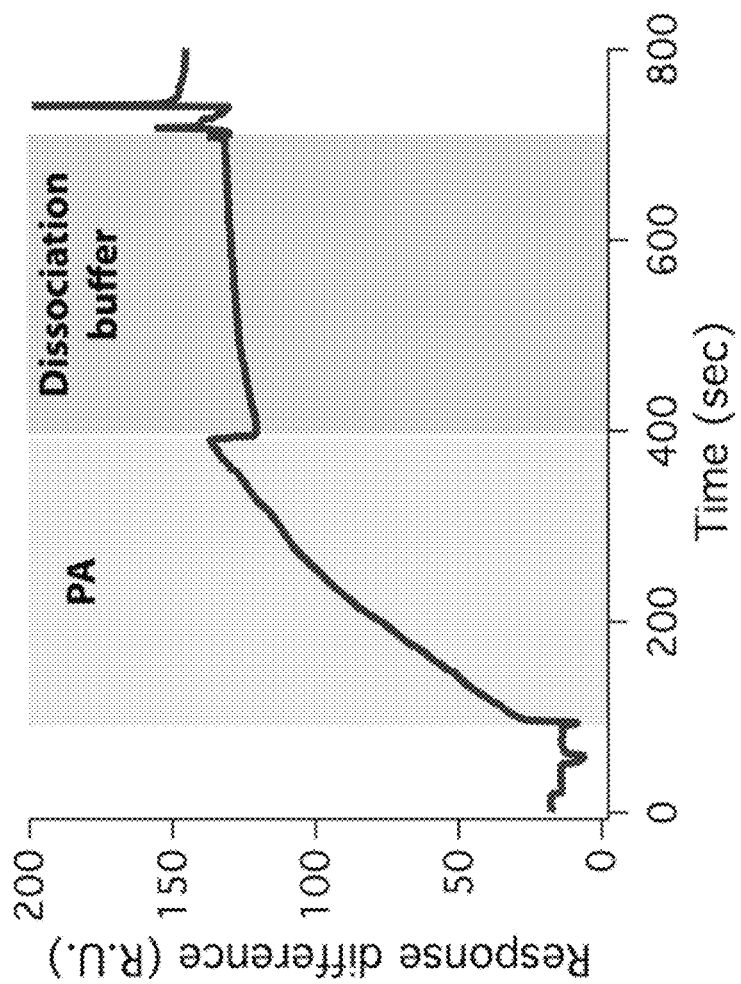
FIGS. 4A-B. As a background control for the surface plasmon resonance (SPR) assay, a 1 µM solution of the BMP-2-binding PA was injected a bare NTA-dextran chip, followed by an injection of the dissociation buffer. The BMP-2-binding PA solution was prepared at (A) pH 7.4 and (B) pH 8.4 for comparison.
Figure 4A:
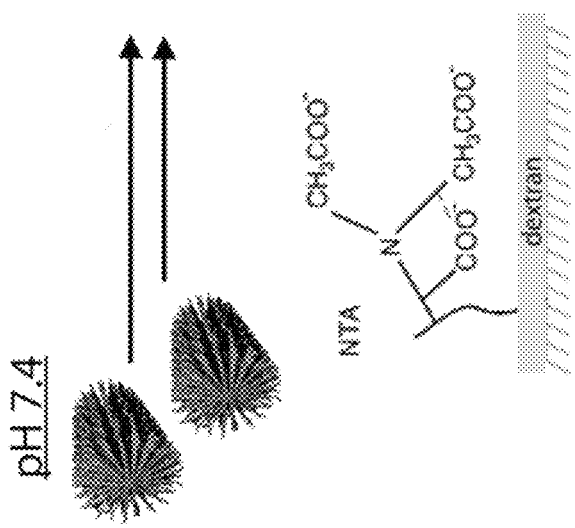
Figure 4B:
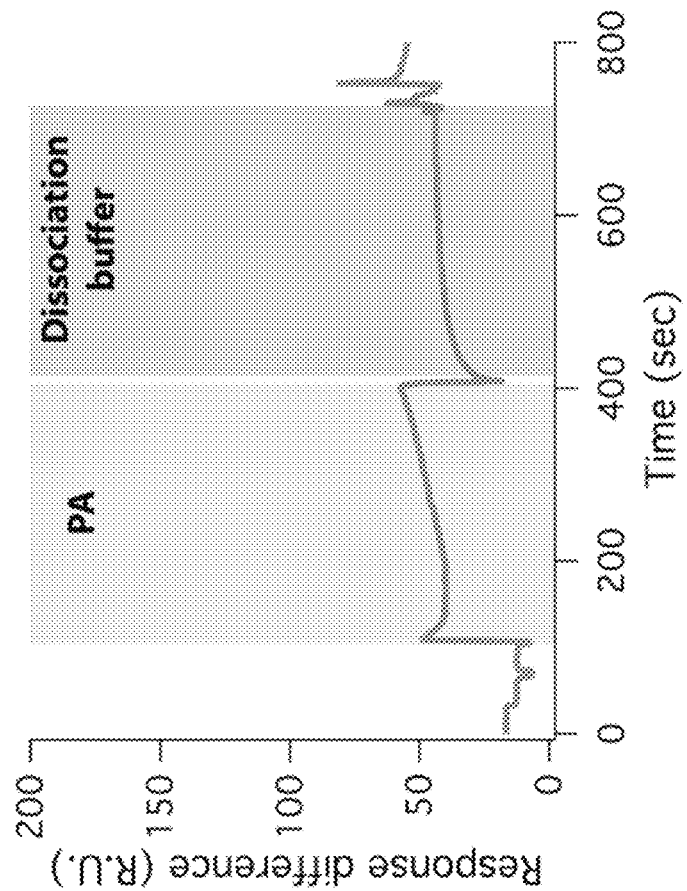
Figure 4B:
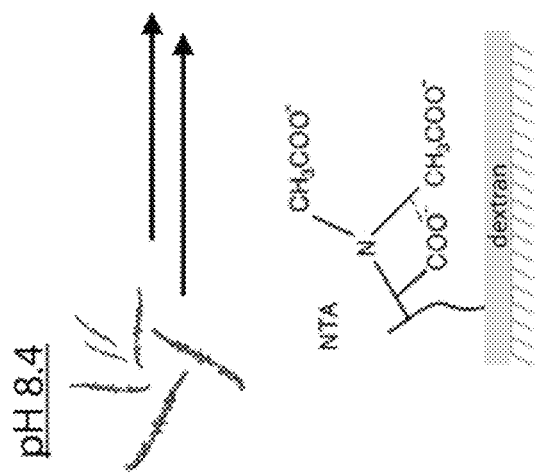

To assess PA nanofiber stability, we measured the critical micelle concentration (CMC) of PAs by Nile red fluorescent probe assay (Boekhoven, A. M. Brizard, P. van Rijn, M. C. A. Stuart, R. Eelkema, J. H. van Esch, Angewandte Chemie (International ed in English) 2011, 50, 12285; herein incorporated by reference in its entirety). At pH 7.4, the supramolecular assembly of the BMP-2-binding PA was detected at above 666 nM (1.5 μg/mL), and that of the diluent PA was detected at above 1 μM (1.2 μg/mL) (FIG. 3). The binding affinities of the PAs to BMP-2 were investigated by surface plasmon resonance (SPR) using hexahistidine-tagged BMP-2 (His-BMP-2) that was immobilized on the surface via nickel (II)-nitrilotriacetic acid ($Ni^{2+}$-NTA) chelation (Knecht, D. Ricklin, A. N. Eberle, B. Ernst, J. Mol. Recognit. 2009, 22, 270; herein incorporated by reference in its entirety). As a control, the BMP-2-binding PA (1 μm, pH 7.4) was injected to a bare NTA-dextran chip, and we observed non-specific binding of the PA to the surface (FIG. 4). It is contemplated that the fibrillar nanostructures can be entangled to the NTA-dextran surface. To circumvent this, the BMP-2-binding PA was prepared at pH 8.4, where more glutamic acid residues are deprotonated to induce greater electrostatic repulsion between the PA molecules, and sonicated the solution to further break up the supramolecular assembly. Consequently, the CMC measurements of the two PAs revealed disruption of the assembly at pH 8.4 (FIG. 3). This BMP-2-binding PA prepared at pH 8.4 also showed minimal binding to the NTA-dextran surface (FIG. 4). Hence, for the SPR analysis, His-BMP-2 we immobilized on the $Ni^{2+}$-NTA surface at pH 7.4 and injected the BMP-2-binding PA or the diluent PA solutions that were prepared at pH 8.4 (FIG. 5). The best fit was obtained by using the 2:1 binding model, which had two dissociation constants: a major dissociation constant ($k_{d,1}$) and a minor dissociation constant ($k_{d,2}$) with the ratio of their contributions ($R_1/R_2$). By using the major dissociation rate and the association rate ($k_a$), it was found that the BMP-2-binding PA had a lower $K_D$ ($3.7 \times 10^{-8}$ M) than the diluent PA ($2.1 \times 10^{-6}$ M), indicating a higher binding affinity to BMP-2.

PA Nanofibers in Solution Enhance BMP-2-Induced Osteogenesis In Vitro

C2C12 pre-myoblast cells have been used as a model to probe the mechanism by which extracellular components such as heparin or heparan sulfate potentiate BMP-2-induced osteoblast differentiation (Zhao et al. *J Biol Chem* 2006, 281, 23246; Bramono et al. *Bone* 2011, 50, 954; herein incorporated by reference in their entireties). C2C12 cells were used to investigate the ability of PA nanofibers to modulate BMP-2 activity in vitro (FIG. 6). Porcine heparin was used as a positive control. Studies verified that the diluent PA, the BMP-2-binding PA, the diluted BMP-2-binding PA, and heparin at 10 μg/mL did not induce cytotoxicity in C2C12 cells (FIG. 7).

Figure 6A:
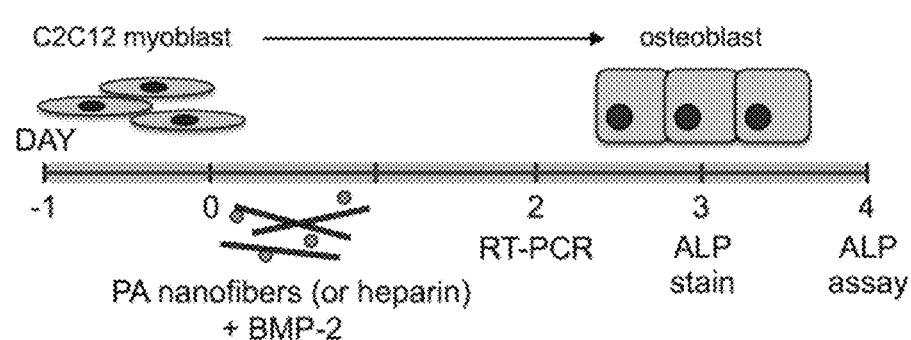
FIGS. 6A-E. BMP-2-induced osteoblast differentiation is enhanced by the BMP-2-binding PA nanofibers in vitro. (A) Schematics of C2C12 cell cultures. Cells were seeded 1 day prior to treatment. On the day of treatment (Day 0), new media was added with the addition of 50 ng/mL BMP-2 along with PAs or porcine heparin at 0, 0.1, 1 or 10 μg/mL. (B) Cells were stained for the presence of ALP after 3 days. A representative scale bar is shown. (C) ALP enzyme activity was measured after 4 days. Measurements were normalized to their respective DNA content, and the final average values from treatments are normalized to control treatment with BMP-2 alone. (D) ALP enzyme activity was measured after 4 days of treatment with PA or heparin at 10 μg/ml without BMP-2. Final average values are normalized to the positive control treatment containing BMP-2. (E) Expression of osteogenic mRNAs after 2 days: Runx2, Osterix (Osx), and osteocalcin (Ocn). PAs and heparin were tested at 10 μg/ml with BMP-2. Each expression was normalized to glyceraldehyde 3-phosphate dehydrogenase (GAPDH), and the average values were normalized to control treatment with BMP-2 alone.
Figure 6B:
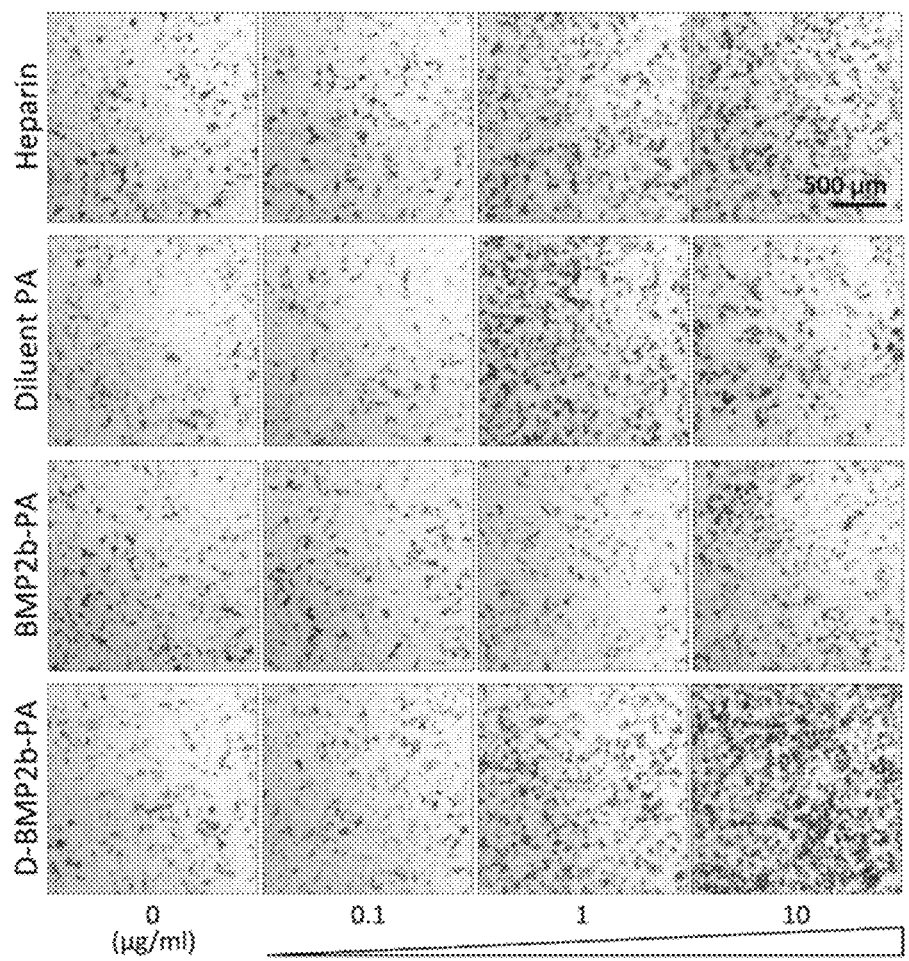
Figure 6C:
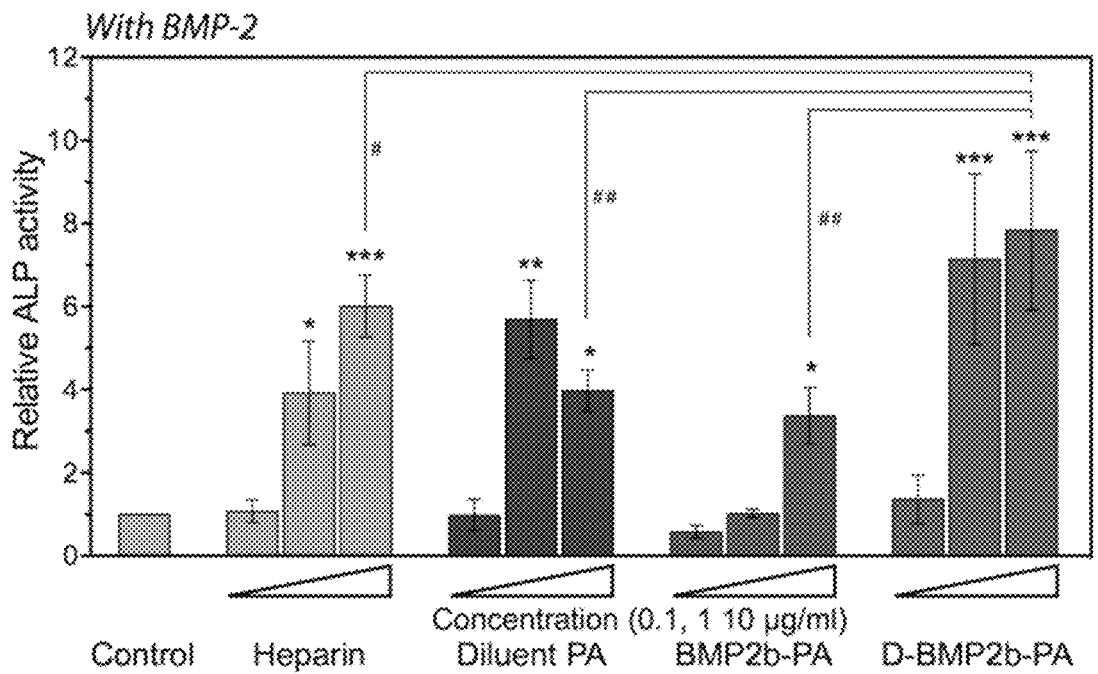
Figure 6D:
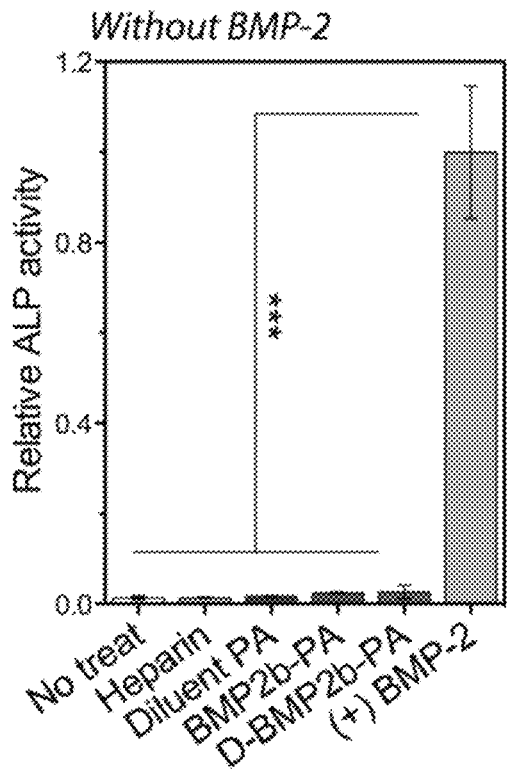
Figure 7A:
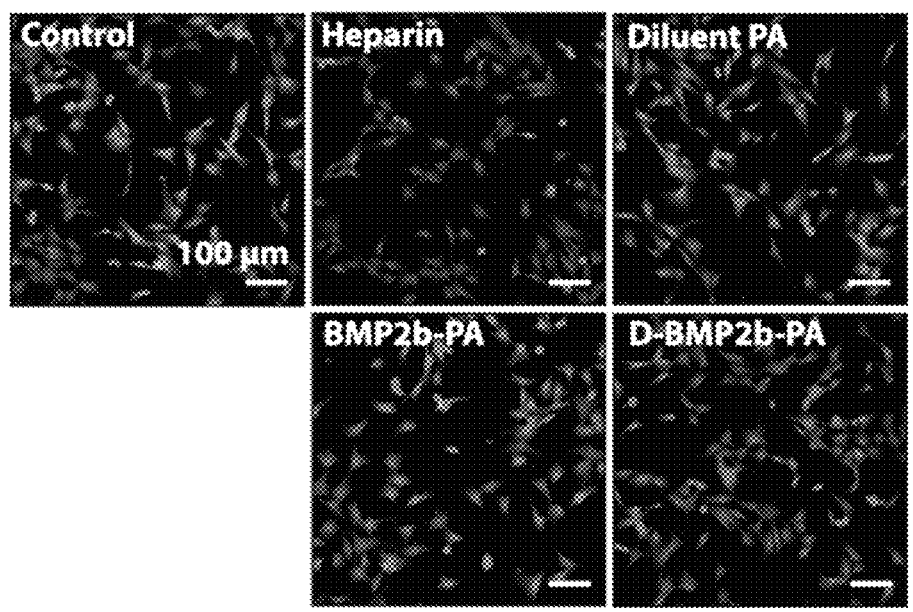
FIGS. 7A-B. The PA systems showed no cytotoxicity on C2C12 cells in vitro. Cells were treated with PAs at a concentration of 10 μg/mL without BMP-2 for 5 h. (A) Live/dead imaging of cells on tissue culture plastic. (B) The presence of lactate dehydrogenase (LDH), a cytosolic enzyme released upon cell lysis, from the cell culture media in each treatment.
Figure 7B:
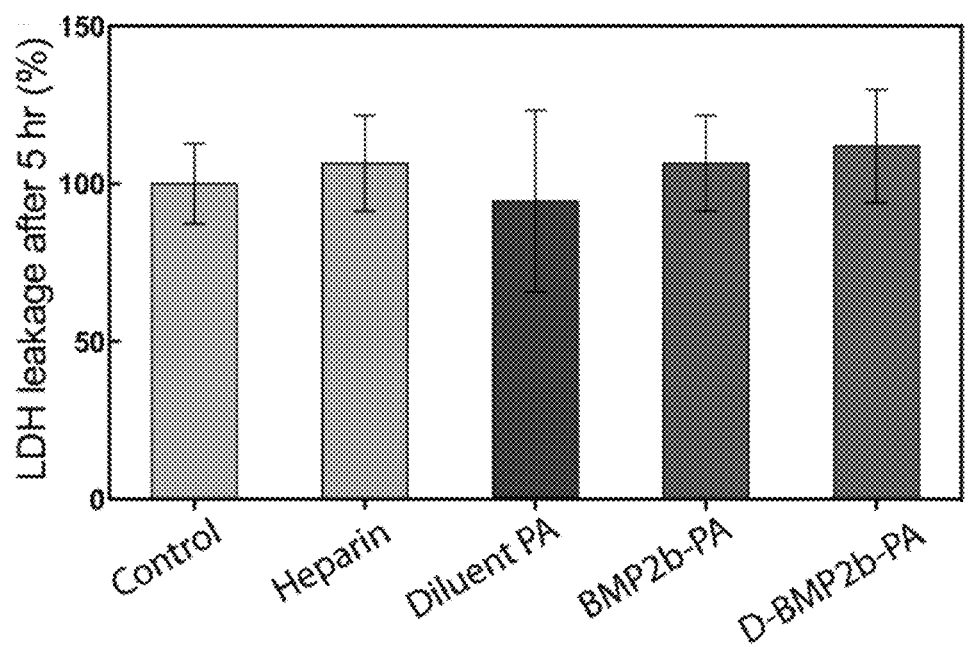
Figure 8:
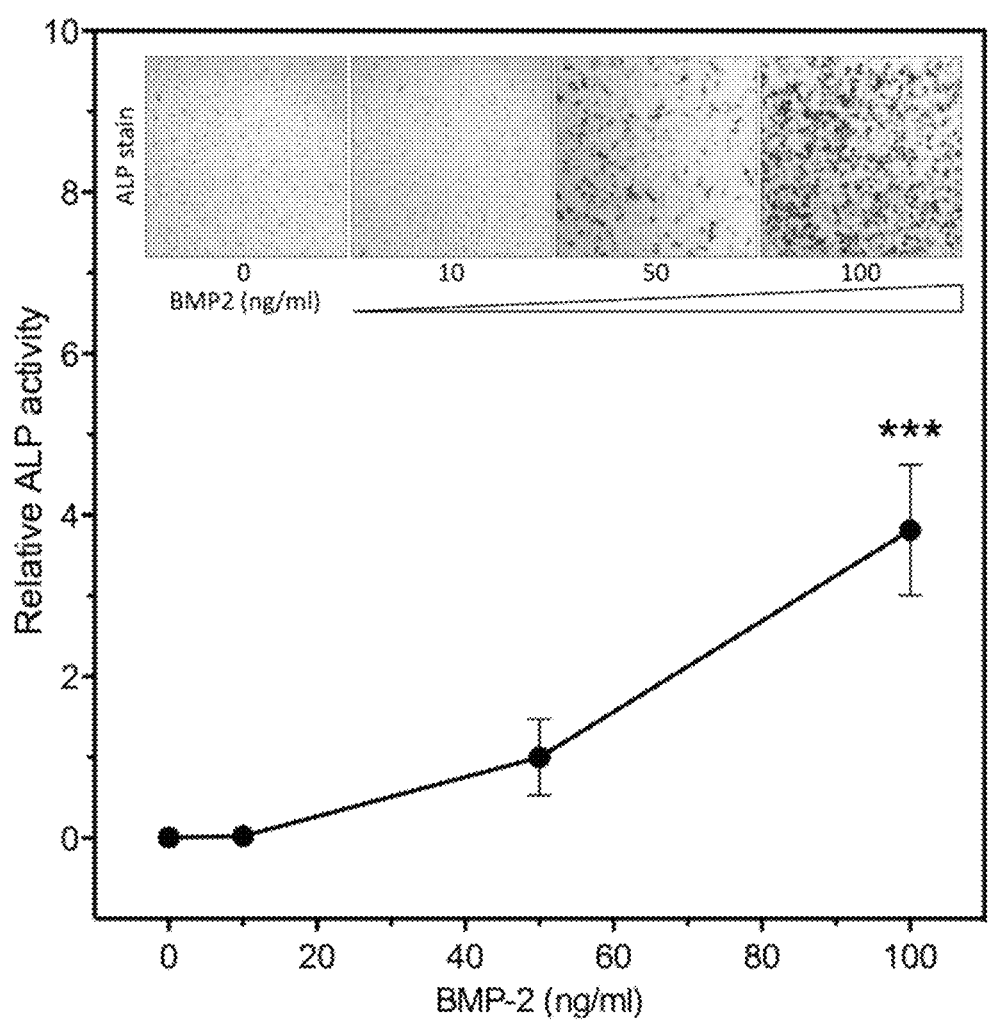
FIG. 8. BMP-2 dose-response in C2C12 osteoblast differentiation. C2C12 cells were seeded for 1 day prior to treatment with BMP-2 at 0, 10, 50, and 100 ng/mL. Alkaline phosphatase (ALP) was stained after 3 days of treatment as a marker for osteoblasts (inset). ALP enzyme activity was measured after 4 days (graph). Measurements were normalized to their respective DNA content, and the final average values from each treatment are normalized to BMP-2 dose at 50 ng/ml.

Experiments were conducted during development of embodiments of embodiments described herein to compare the effect of PA nanofibers on alkaline phosphatase (ALP) activity, a marker for osteoblast differentiation (FIG. 6A). Based on dose-response pilot for the effect of BMP-2-mediated C2C12 differentiation into osteogenic cells (FIG. 8), 50 ng/mL BMP-2 was selected as a fixed treatment condition for our in vitro studies. Enzymatic labeling revealed a directly proportional association of the number of ALP-positive cells with heparin concentrations up to 10 μg/mL (FIG. 3B, top row). An increased number of ALP-positive cells was also observed when treated with the diluent PA, which lacks the protein-binding moiety (FIG. 6B, second row). Treatment with exogenous BMP-2 in the presence of the BMP-2-binding PA also showed a slight increase in the number of ALP-positive cells at 10 μg/mL PA concentration (FIG. 6B, third row). Interestingly, it was observed that the diluted BMP-2-binding PA exhibited the highest increase in the number of ALP-positive cells after 3 days of treatment (FIG. 6B, bottom row). Quantification of the ALP activity of C2C12 cells and demonstrated that all PA systems significantly increased ALP activity at 1 and 10 μg/mL in comparison to BMP-2 alone (FIG. 6C). At a dose of 10 μg/mL, the diluted BMP-2-binding PA resulted in significantly higher ALP activity than heparin ($P<0.05$), as well as the diluent PA or the BMP-2-binding PA alone ($P<0.01$). Without the presence of BMP-2, it was observed that PAs and heparin did not promote ALP expression in these cells (FIG. 6D). Furthermore, a PA similar in design to the diluent PA was tested but with positively charged lysine residues, and no enhancement of BMP-2-induced ALP activity was observed at the same PA concentration range (FIG. 9). Overall, it was observed that the negatively charged residues on the PA molecules played a crucial role in augmenting BMP-2-induced osteoblast differentiation and the addition of the BMP-2-binding epitope at an appropriate density further enhanced the potency of the growth factor.

Figure 6E:
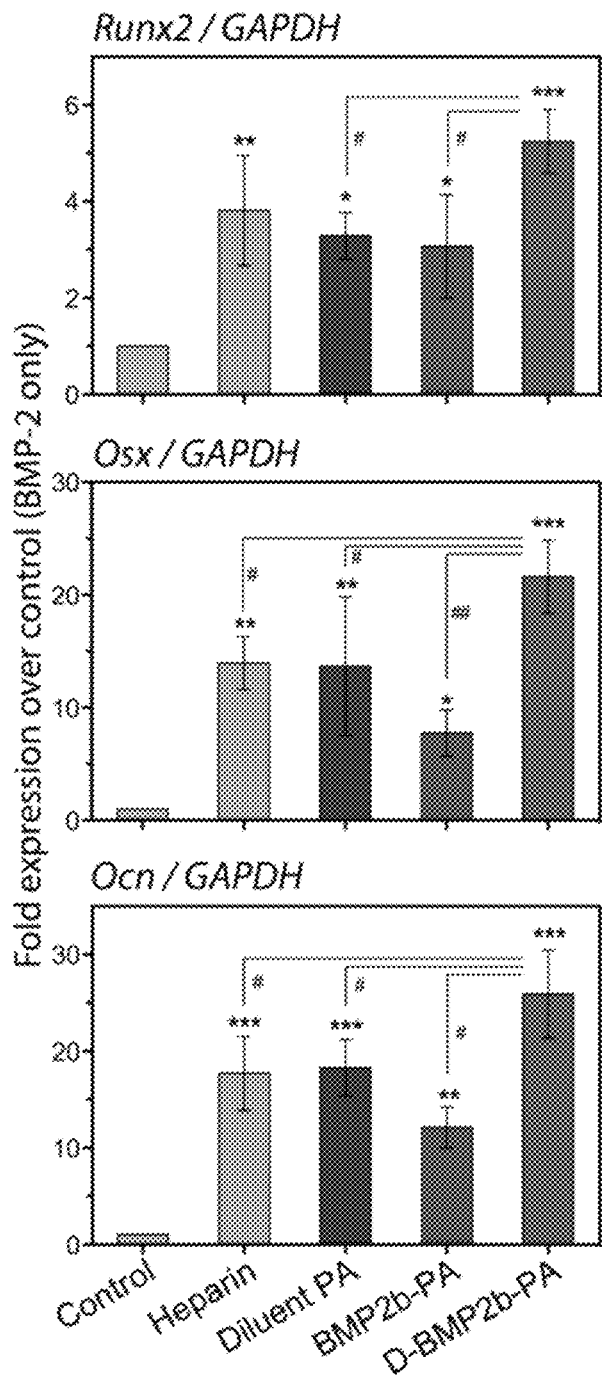

In order to further assess the effect of PA systems on BMP-2 activity, changes in the expression of osteogenic genes in C2C12 cells was examined, including Runx2, Osterix (Osx), and osteocalcin (Ocn) (FIG. 6E). The mRNA levels from treatments with BMP-2 in combination with the diluent PA, the BMP-2-binding PA, the diluted BMP-2-binding PA, and heparin at 10 µg/mL led to enhanced osteoblastic differentiation relative to BMP-2 alone. The diluted BMP-2-binding PA system showed the highest increase in Runx2, Osx, and Ocn relative to growth factor alone (P<0.001). Furthermore, the diluted BMP-2-binding PA led to gene expressions that were significantly higher (P<0.05) than the BMP-2-binding PA or diluent PA alone.

PA Nanofiber Gel Prolongs Growth Factor Retention

In order to develop therapeutic materials to promote bone regeneration, the ability of the BMP-2-binding PA system to form gels and their BMP-2 release kinetics were tested (FIG. 10). Since the BMP-2-binding PA when used alone showed the least enhancement of BMP-2-induced activity in C2C12 cells, only the diluted BMP-2-binding PA and the diluent PA were further characterized. Indeed, both PAs were able to form self-supporting gels upon mixing with calcium chloride solution (FIG. 10A). Scanning electron microscopy (SEM) verified the presence of nanofibers in these gels (FIG. 6B). Rheological analysis confirmed that both PAs at 10 mg/mL (or 1 wt %) exhibited gel-like properties with storage moduli (G') approximately one order of magnitude higher than the loss moduli (G") across the tested frequency range of 1-100 $s^{-1}$ (FIG. 6C). When comparing the two PA systems, the diluted BMP-2-binding PA had G' and G" values that were lower than those of the diluent PA, respectively. BMP-2 release from these PA gels was evaluated via ELISA (FIG. 6D). Upon initial loading of 50 ng BMP-2, it was observed that a prolonged retention of the cytokine from both the diluted BMP-2-binding PA and the diluent PA gels in comparison to a conventional absorbable collagen sponge. After 28 days in vitro, the amount of BMP-2 released from the collagen sponge was approximately 4.2±0.3 ng, which was more than double the amount of protein released from the diluted BMP-2-binding PA gel (1.6±0.1 ng) and the diluent PA gel (1.3±0.1 ng). Furthermore, we tested the ability of the PA gels to capture the growth factor from the medium that contained 25 ng BMP-2 (FIG. 6E). After 4 h in vitro, the amount of BMP-2 bound on the diluted BMP-2-binding PA gel (15.5±5.5 ng) was significantly greater than that on the diluent PA gel (6.4±0.7 ng). After 16 h, no significant difference was found in the amount of growth factor bound on the two gels.

BMP-2-Binding PA Gel Augments Spinal Fusion

Figure 11:
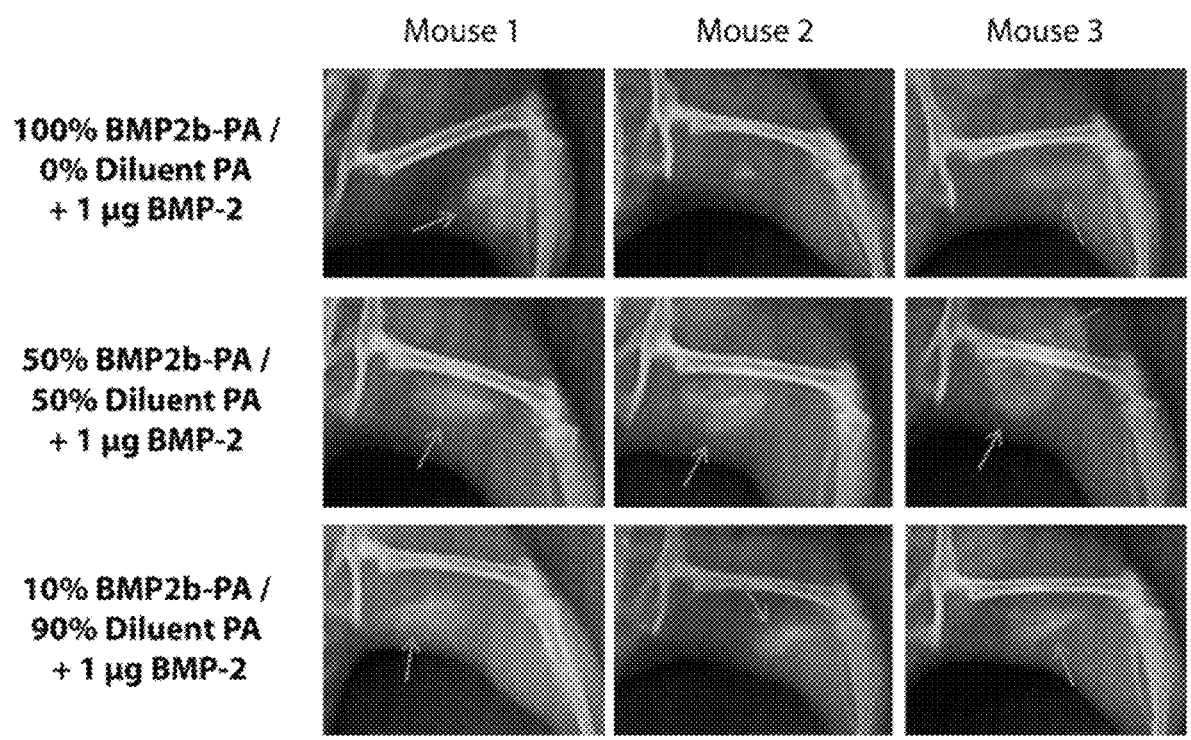
FIG. 11. Ectopic bone formation in mouse leg muscles following injection of 1 μg BMP-2 in the BMP-2-binding PA gels. PA gels were prepared with varying ratios of the BMP-2-binding PA to the diluent PA (100%, 50%, and 10% BMP-2-binding PA), and radiographs were taken at 2-week time point. Qualitatively, the animals treated with the 50% BMP-2-binding PA showed the presence of ectopic bone that was overall larger and more localized than the animals treated with either the 100% of the 10% BMP-2-binding PA gels.

In order to verify in vivo the efficacy of the BMP-2-binding PA to promote BMP-2-induced osteogenesis and to identify the ideal proportions of the binding and diluent PAs, a mouse muscle pouch model was utilized to assess ectopic bone formation following implantation of various gel formulations impregnated with 1 µg BMP-2. After 2 weeks, radiographs revealed that the 50%-diluted BMP-2-binding PA gel exhibited new bone that was qualitatively more localized and larger in size than those formed by the 10%-diluted BMP-2-binding PA gel or the 100% BMP-2-binding PA gel (FIG. 11).

With the objective of investigating the translational potential of the supramolecular nanofibers, the ability of the BMP-2-binding PA system to promote bone formation and spine arthrodesis was evaluated in a well-established rat posterolateral lumbar intertransverse spinal fusion model (FIG. 12). In this model the bone healing process is initiated at the fusion bed site between L4 and L5 transverse processes (Hsu et al. J Bone Joint Surg Am 2008, 90, 10430.; Hsu et al. J Orthop Res 2011, 29, 1812; herein incorporated by reference in their entireties). Based on both in vitro as well as the ectopic bone formation results, the 50%-diluted BMP-2-binding PA was selected as the treatment condition for the spinal fusion study. Hence, the diluted BMP-2-binding PA gel, the diluent PA gel, and the collagen sponge were preloaded with BMP-2 doses of 0, 0.1, to 1 µg per animal and applied to bridge the decorticated L4 and L5 transverse processes (Table 1). Eight weeks post-treatment, blind manual palpation scores demonstrated that treatments with the diluted BMP-2-binding PA gel elicited the highest fusion scores relative to other conditions with equivalent doses of BMP-2 (FIG. 12A). It was observed that the diluted BMP-2-binding PA with 1 µg BMP-2 was the only treatment that showed an average fusion score (2.4±0.0) that was comparable to treatment with 10 µg BMP-2 in collagen sponge (clinical positive control; 2.2±0.1). When preloaded with 1 µg BMP-2, the diluted BMP-2-binding PA gel resulted in a significantly higher fusion score (P<0.001) than the diluent PA gel (1.4±0.2) or collagen sponge (1.0±0.2). At 0.1 µg BMP-2, the diluted BMP-2-binding PA gel elicited an average fusion score (0.6±0.2) was significantly higher (P<0.01) than the effectively zero fusion score for a collagen sponge. At this dose of growth factor, the average fusion score of the diluent PA gel (0.4±0.1) was also significantly higher (P<0.05) than that of the collagen sponge. It was observed that the diluted BMP-2-binding PA gel alone without any exogenous growth factor elicited a significantly greater fusion score (0.6±0.2) than the other treatments (P<0.05).

TABLE 1

Animal groups for the rat posterolateral lumbar intertransverse spinal fusion model study.

| | | n | |
|---|---|---|---|
| Treatment | Total | Analyzed w/manual palpation | Analyzed w/µCT |
| I. D-BMP2b-PA | | | |
| 0 µg BMP-2 | 12 | 12 | 5 |
| 0.1 µg BMP-2 | 12 | 12 | 4 |
| 1 µg BMP-2 | 12 | 12 | 12 |
| II. Diluent PA | | | |
| 0 µg BMP-2 | 12 | 12 | 0 |
| 0.1 µg BMP-2 | 12 | 12 | 0 |
| 1 µg BMP-2 | 12 | 12 | 9 |
| III. Collagen scaffold | | | |
| 0 µg BMP-2 | 8 | 8 | 3* |
| 0.1 µg BMP-2 | 12 | 12 | 0 |
| 1 µg BMP-2 | 12 | 12 | 8 |
| 10 µg BMP-2 (+) | 8 | 8 | 0 |

*analyzed as threshold values for µCT analysis

Fusion rates followed the same trend from average fusion scores, with the diluted BMP-2-binding PA gel generally outperforming the other treatments at all doses of BMP-2 (FIG. 12B). When preloaded with 1 µg BMP-2, the collagen sponge, the diluent PA gel, and the diluted BMP-2-binding PA gel elicited fusion rates of 67%, 75%, and 100%, respectively. It is notable that the 100% fusion rate seen with 10 µg BMP-2 on collagen sponge (positive control) was achievable with only 1 µg BMP-2 when delivered in the diluted BMP-2-binding PA gel. With 0.1 µg BMP-2, both the collagen sponge and diluent PA gel resulted in fusion rates of 0%, whereas the diluted BMP-2-binding PA gel resulted in a fusion rate of 33%. Interestingly, as seen in the fusion score analysis, we observed a 42% fusion rate when treated with the diluted BMP-2-binding PA without the addition of BMP-2.

Figure 12D:
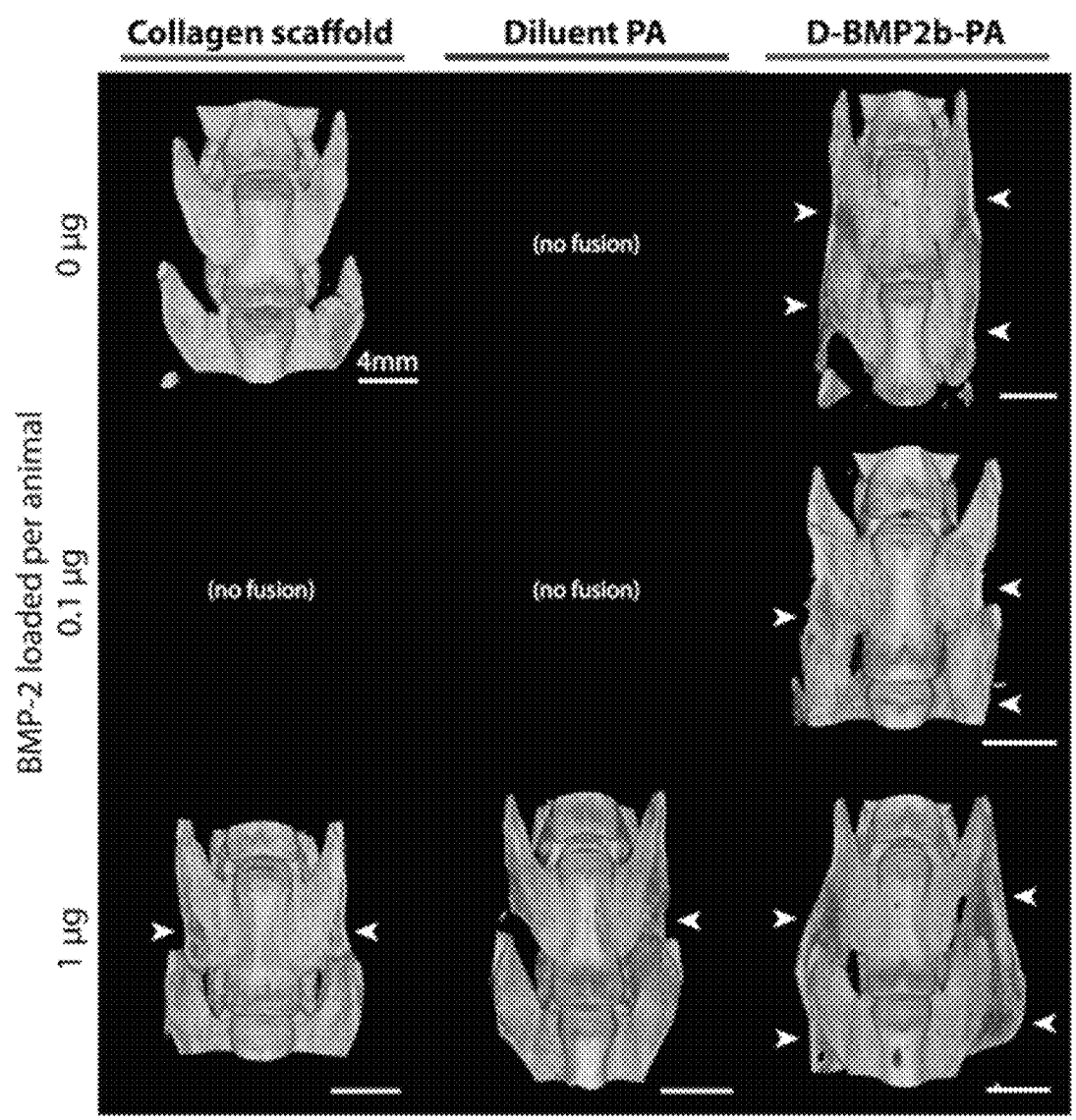
Figure 13:
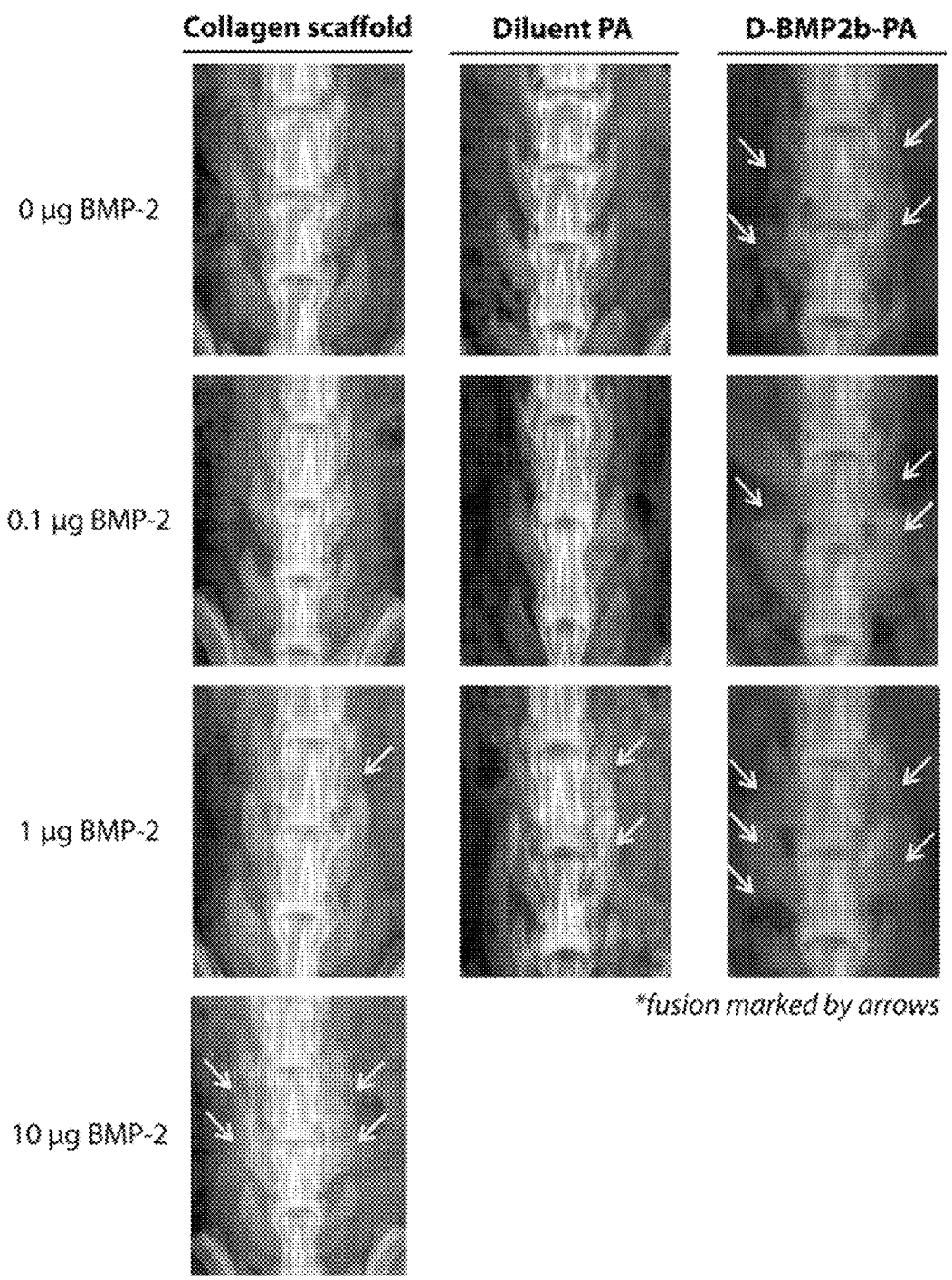
FIG. 13. Representative dorsal-ventral plain radiographs at 8-week time point of specimens with successful spinal fusion that was determined based on manual palpation scores (as shown in FIG. 4). Treatment with the diluted BMP-2-binding PA showed new bone formation within the fusion mass (yellow arrows) that was not observed as consistently in other treatment groups.

In order to quantify the amount of new bone formed in the transverse processes, quantitative analysis was performed of µCT reconstructions of the samples that were successfully fused (Table 1). In all of the conditions, the diluted BMP-2-binding PA gel with 1 µg BMP-2 had by far the highest mean volume of new ossified tissue (460.6±65.3 mm$^3$) relative to all other treatments (FIG. 12C). This mean volume was significantly greater (P<0.001) than those observed in animals treated with 1 µg BMP-2 in the diluent PA gel (112.7±41.4 mm$^3$) or in the collagen sponge (135.9±15.9 mm$^3$) by at least a factor of three. In addition, treatment with 0.1 µg BMP-2 delivered in the diluted BMP-2-binding PA gel exhibited on average new bone volume (162.1±54.5 mm$^3$) that was similar to those treated with BMP-2 at a dose ten-fold higher (10 µg) in the diluent PA gel or the collagen sponge. Following the trend from the manual palpation analysis, it was also observed by µCT evaluation the presence of new bone formed by the diluted BMP-2-binding PA gel that had no exogenous BMP-2 (212.2±58.2 mm$^3$), and this mean volume was comparable to those in animals treated with either the diluent PA gel or collagen sponge at all doses of BMP-2. Representative images from 3-D µCT rendering revealed that in all of the animals with successful fusion, the diluted BMP-2-binding PA gel was the only treatment that exhibited some degree of bilateral bridging of the L4 and L5 transverse processes at all BMP-2 doses, including the 0 µg dose (FIG. 12D). Dorsal-ventral radiographs of these samples taken at 8 weeks post-treatment verified fusion observed in µCT rendering (FIG. 13).

Figure 14:
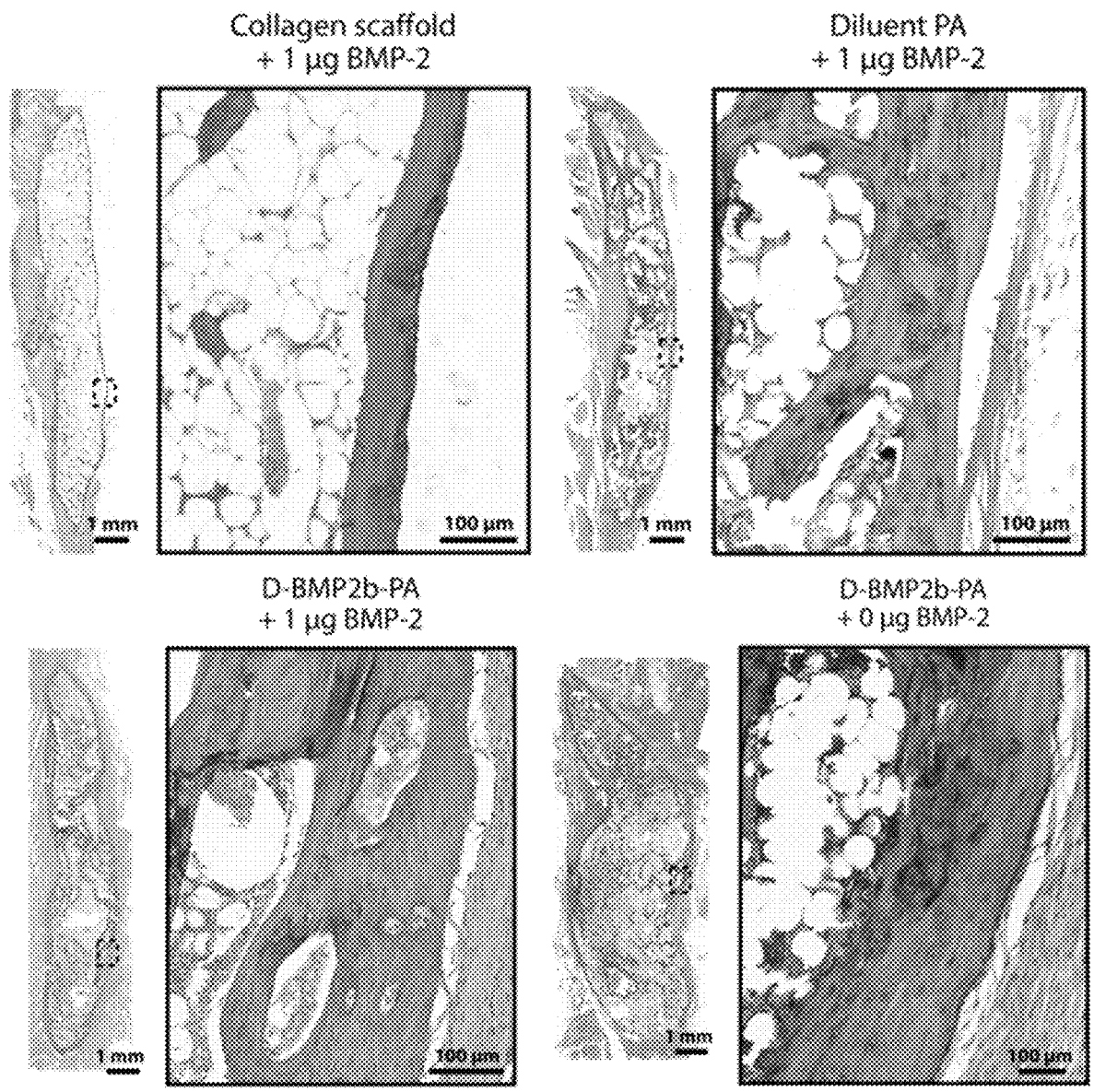
FIG. 14. Representative sagittal cross-sectional images of fused L4-L5 posterolateral spine specimens 8 weeks after surgery with hematoxylin and eosin. The box shows a higher magnification image of the inset indicated on the dorsal side of the fusion bed.

Histological analysis of spine specimens, using hematoxylin and eosin staining, confirmed the results from µCT measurements (FIG. 14). Treatment with the diluted BMP-2-binding PA in the presence of 1 µg BMP-2 demonstrated robust fusion mass, and the cortical trabeculae from this sample was thicker and more abundant when compared to other groups containing 1 µg BMP-2. No evidence of a local inflammatory response was found in any of the specimens.

Example 2

Materials and Methods

Materials

C2C12 myoblast cell line and DMEM were purchased from American Type Culture Collection (ATCC, Manassas, Va.). C2C12 cells were used at passages 3 to 6. Heat inactivated HyClone fetal bovine serum (FBS) was purchased from Thermo Scientific (Hanover Park, Ill.). Commercial porcine mucosa-derived heparin sodium was purchased from Celsus Laboratories (Cincinnati, Ohio). Recombinant human BMP-2 was obtained from Medtronic Sofamor Danek (Minneapolis, Minn.).

PA Synthesis and Preparation

PAs were synthesized using standard 9-fluorenyl methoxycarbonyl (Fmoc) solid-phase peptide synthesis and purified by reverse phase high performance liquid chromatography (HPLC) in a water-acetonitrile gradient, each containing 0.1% v/v ammonium hydroxide (NH4OH). PAs were synthesized with the following amino acid sequences and a carbon alkyl tail covalently attached: C12-(K)V3A3E3-SGGGYPVHPST-NH2 (BMP2b-PA) (SEQ ID NO:4) and C16-V3A3E3-COOH (diluent PA) [21,32]. Purified PA was stored at −20° C. until use. For all studies, lyophilized BMP2b-PA and diluent PA were separately reconstituted in sterile 2 mM NH4OH at desired concentrations (wt %) and sonicated for 30 min. In order to space BMP-2-binding segments on the surface of the supramolecular nanofibers, the diluted BMP2b-PA (D-BMP2b-PA) was prepared by mixing equal volumes of BMP2b-PA and diluent PA at equal concentrations, followed by 30 min sonication; the final PA concentration of D-BMP2b-PA therefore remained the same as prior to mixing. All PAs were freshly dissolved for each experiment.

Circular Dichroism (CD)

CD was performed on a J-815 CD spectrophotometer (Jasco, Easton, Md.). PA samples were prepared at 1 wt %, then diluted to 0.01 wt % in 0.1 mM CaCl2. Measurements were collected at 37° C. over a wavelength range of 280-180 nm with a 0.5 nm step size and five accumulations per scan.

Cryogenic Transmission Electron Microscopy (Cryo-TEM)

Cryo-TEM was performed on a JEOL 1230 microscope (JEOL USA, Peabody, Mass.) according to a previously described protocol [22]. PA samples were prepared at 1 wt %, then diluted to 0.5 wt % in 0.1 mM CaCl2 for imaging.

Surface Plasmon Resonance (SPR) Measurements

The SPR measurements were performed using a Biacore 3000 instrument (GE Healthcare, Pittsburgh, Pa.) equipped with a NTA Sensor Chip (GE Healthcare) at 25° C. HBS-P eluent buffer and HBS-EP dispenser buffer were purchased from GE Healthcare. NiCl-2 solution (500 µM in eluent buffer), elution buffer (300 mM imidazole and 500 mM NaCl in water), and regeneration buffer (10 mM HEPES, 150 mM NaCl, 0.005% polysorbate 20, 350 mM EDTA at pH 7.4) were prepared according to Biacore specifications. Human recombinant BMP-2 with hexahistidine-tag fused at the C-terminus (AdipoGen, San Diego, Calif.) was initially reconstituted in PBS at 20 µg/ml, and diluted to 500 nM in eluent buffer.

Binding Experiments

Ni$^{2+}$ was first loaded on the NTA chip for 5 min at a flow rate of 20 µl/min, and then His-BMP-2 for 1.25 min at 4 µl/min. Afterwards, each PA sample was injected for 2 min at 20 µl/ml, followed by 5 min dissociation at 20 µl/ml. The flow cell was regenerated using the elution buffer and the regeneration buffer, each for 2 min at 100 µl/ml. The surface was further washed with 0.5% SDS in water for 12 sec at 100 µl/ml. PA samples were horn-sonicated and diluted in eluent buffer that was adjusted to pH 8.5 to prevent non-specific binding to NTA. PA solutions were injected to a blank NTA flow cell without Ni2+ or His-BMP-2 was used as a reference cell. To compare binding affinity of the PAs, the sensograms were processed and analyzed with BIAevaluation 4.1 software. The sensogram from blank injection was subtracted from the PA sensograms, and the apparent equilibrium dissociation constant KD was determined using 2:1 binding model, which assumes bivalent analyte interaction with two dissociation constants kd,1 and kd,2, where kd,1 is more dominant.

Cell Culture

Figures 5A, 5B:
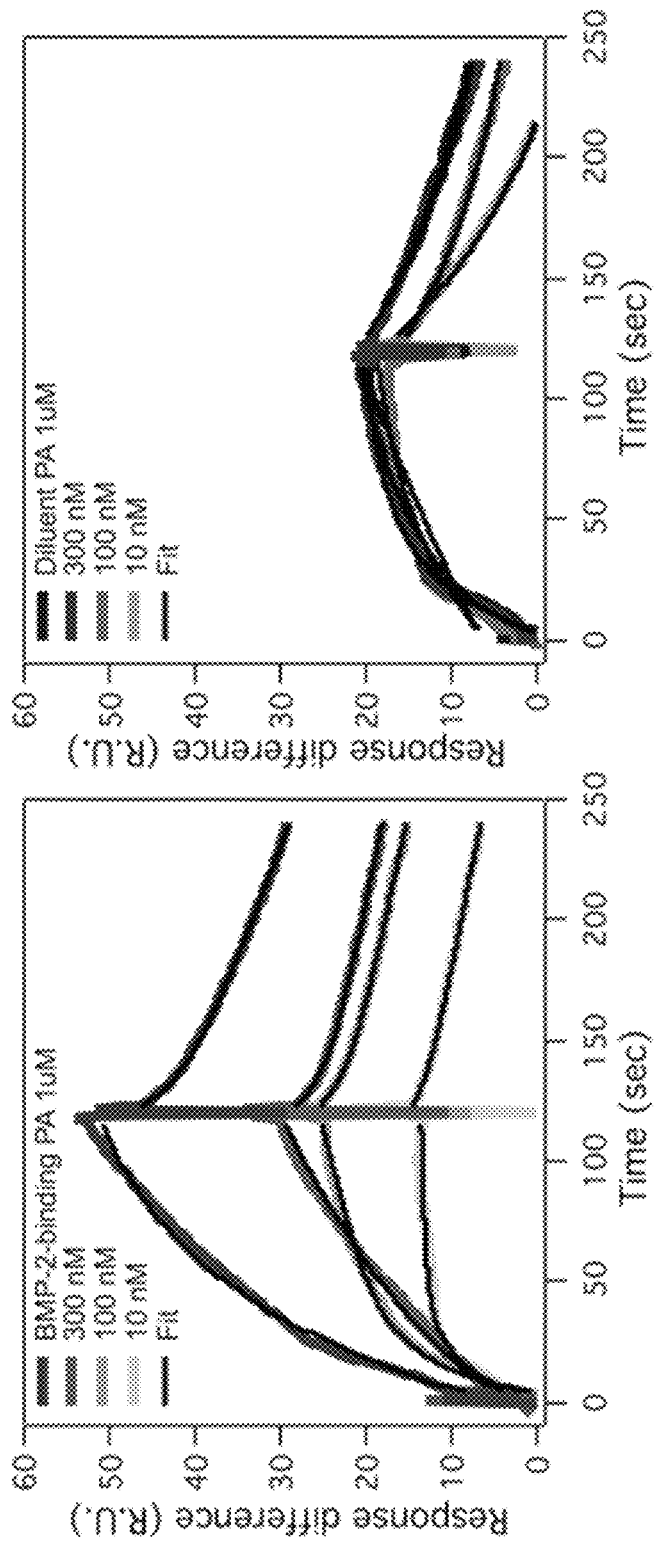
FIGS. 5A-B. Binding affinities of the PA systems to BMP-2 using surface plasmon resonance. (A) Overlay plots showing the binding of the BMP-2-binding PA (green) and the diluent PA (blue) in subsequent dilutions. The calculated fit was obtained using the 2:1 binding model with constants shown in (B).

C2C12 pre-myoblasts were maintained and treated with BMP-2 as depicted in FIG. 5A. C2C12 cells were seeded at 2×10⁴ cells/cm² in 24-well plates in growth media (DMEM with 10% heat-inactivated FBS and 100 U/mL penicillin/streptomycin, P/S) 1 day before treatment. On the following day (Day 0), growth media was replaced with 900 µL maintenance media (growth media with 2.5% FBS) and 100 µL treatment media containing BMP-2 with heparin or PAs. Preparation of the treatment media was as follows: 2.5 µL of BMP-2 stock (20m/mL) was mixed with 5 µL of heparin or PA stock solutions (0.02, 0.2, or 2 mg/mL), incubated for 5 min on ice, then mixed with DMEM (100 U/mL P/S) to a final volume of 100 µL, followed by 5 min incubation on ice. For treatments with BMP-2 only, the treatment media was prepared according to the method described except without heparin or PAs. Final working concentrations were 50 ng/mL BMP-2 and a range of 0.1, 1, to 10 µg/mL heparin or PAs.

Alkaline Phosphatase (ALP) Stain

The presence of ALP was stained as a marker for osteoblast differentiation on day 3 by enzymatic labeling described by Mason and Woolston (herein incorporated by reference in its entirety). C2C12 cell layer was fixed with 4% paraformaldehyde (PFA) for 30 s, washed with PBS three times, and stained for 1 h with Naphthol AS-MX phosphate (Sigma-Aldrich, St. Louis, Mo.) and Fast Blue BB salt (Sigma-Aldrich) in 0.1M Tris-HCl at pH 8.2, followed by washing with PBS.

Alkaline Phosphatase (ALP) Activity Assay

ALP activity from C2C12 cell layer was measured using QUANTI-Blue ALP substrate (InvivoGen, San Diego, Calif.). On Day 4, C2C12 cell monolayers were lysed on ice with 100 µL lysis buffer (20 mM Tris-HCl, 1 mM EDTA, 150 mM NaCl, 1 mM MgCl2, 1% NP-40 (Igepal), and 5% glycerol at pH 7.9) containing Halt Protease Inhibitor Cocktail (Thermo Scientific). Supernatants were collected into a sterile centrifuge tube and spun at 13,200 rpm on microcentrifuge at 4° C. for 3 min. Afterwards, 20 µL of the supernatant was placed into a flat-bottom 96-well plate and mixed with 180 µL QUANTI-Blue ALP substrate (in duplicates). The plate was incubated at 37° C. for 18 h and absorbance was measured at 630 nm on SpectraMax M5 Microplate Reader (Molecular Devices, Sunnyvale, Calif.). In addition, 5 µL of the collected C2C12 cell supernatant was diluted with 95 µL TE buffer and mixed with 100 µL Quant-iT PicoGreen dsDNA reagent (Invitrogen) in a clear-bottom, black 96-well plate to measure the concentration of dsDNA (in triplicate). The absorbance values from QUANTI-Blue ALP assay was normalized by the amount of dsDNA in each sample, and the resulting values from heparin and PA treatments were normalized to control (BMP-2 only) to represent the relative fold increase (n=3, in triplicate experiments).

Real-Time PCR

C2C12 cells were treated with 50 ng/ml BMP-2 in the presence of 10 µg/mL heparin or PAs until Day 2, and the osteogenic gene expression levels were determined by real-time PCR as described by Zhao et al. (n=4, in triplicate experiments) [36]. Briefly, total RNAs were isolated from cells using TRIzol (Invitrogen) and reverse-transcribed using iScript Reverse Transcription Supermix (Bio-Rad, Des Plaines, Ill.). PCR amplification was analyzed with iQ5 Real-Time PCR Detection System (Bio-Rad) using iQ SYBR Green Supermix (Bio-Rad) and the following primers: Runx2 types II & III (Runx2), 5'-ATGCTTCATTCAT-TCGCCTCACAAAC-3' (SEQ ID NO:5) and 5'-CCAAAAGAAGCTTTGCTG-3' (SEQ ID NO:6); Osterix (Osx), 5'-TTAAGCTTGCGTCCTCTCTGCTTGA-3' (SEQ ID NO:7) and 5'-TTTCTAGATCA-GATCTCTAGCAGGTT-3'(SEQ ID NO:8); Osteocalcin (Ocn), 5'-CAAGTCCCACACAGCAGCTT-3'(SEQ ID NO:9) and 5'-AAAGCCGAGCTGCCAGAGTT-3'(SEQ ID NO:10); and Glyceraldehyde-3-phosphate dehydrogenase (GAPDH), 5'-TGAAGGTCGGTGTGAACGGATTGGC-3' (SEQ ID NO:11) and 5'-CATGTAGGCCATGAGGTCCAC-CAC-3'(SEQ ID NO:12) (IDT, Coralville, Iowa). For PCR amplification, cDNA was denatured at 94° C. for 5 min, then underwent 40 repeated cycles at 94° C. for 45 s, annealing at 55° C. for 1 min, and extension at 68° C. for 1 min, followed by 79 repeated cycles at 55° C. for 30 s for generation of a melting curve. Expression values of Runx2 II, Osx, and Ocn were normalized to the respective GAPDH levels, and all treatments were normalized to control (BMP-2 only) treatment in order to represent relative fold increase.

PA Nanofiber Gel Assembly

Diluent PA, BMP2b-PA, and D-BMP2b-PA solutions were prepared at 2 wt %. PA gel (1 wt % PA) was formed by mixing equal volumes of 2 wt % PA and 20 mM CaCl₂). Where recombinant human BMP-2 was incorporated into the PA gel, the protein was first combined with 20 mM CaCl2 solution prior to mixing with PA.

Scanning Electron Microscopy (SEM)

PA nanofiber gels were fixed in 4% paraformaldehyde, dried, then visualized with a Hitachi S-4800 II FE-SEM (Hitachi High Technologies America, Dallas, Tex.).

Rheology

Rheological measurements were performed using MCR-300 rheometer (Anton Parr, Graz, Austria) with a 25 mm parallel plate at 0.5 mm gap distance and 37° C. stage temperature. To initiate gel formation, 20 µL of 0.2 M CaCl2 was added to 140 µL of 1.25 wt % PA solution on the rheometer plate. After a 30 min equilibration period at 37° C., the samples were tested at a constant strain of 0.5% over angular frequency range of 1-100 s−1 (n=3).

Growth Factor Release Kinetics from PA Gels

Absorbable collagen sponges cut to 0.135 cm3 as measured using digital microcalipers with a resolution of 0.01 mm were placed into microfuge tubes and pre-loaded with 50 ng of recombinant human BMP-2. Both the diluted BMP-2-binding PA gels and the diluent PA gels were prepared to a final volume of 40 µl with 50 ng of BMP-2 as described above. After a 20 min incubation period, 700 µl of release media (0.1% BSA in PBS) was applied to each tube. Tubes were pulse-spun, and 300 µl of release media was collected from each. An additional 300 µl of fresh release media was applied to the scaffolds, and the tubes were pulse-spun. The second 300 µl aliquot of release media was collected from each tube and combined with the original aliquot to obtain a 600 µl supernatant sample at day 0. A final addition of 300 µl fresh release media was applied to each tube, and scaffolds were incubated at 4° C. until the next time point. At increasing time points out to 28 days, the same procedure was performed, with two aliquots of release media removed for future analysis and fresh media subsequently replaced. All aliquots were frozen at −80° C. until quantitation. BMP-2 was quantified in the collected samples using a sandwich ELISA (R&D Systems, Minneapolis, Minn.) per the manufacturer's instructions.

Growth Factor Capture by PA Gels

Both the diluted BMP-2-binding PA gels and the diluent PA gels were prepared as described above to a final volume of 20 µL inside a 2 mL microcentrifuge tube. After a 10 min incubation period, 1 mL of 25 ng/mL BMP-2 media (0.01% BSA in DMEM) was applied. Tubes were gently inverted ten times and incubated at 37° C. At each time point (4 and 16 h), the tubes were inverted twice and media was collected and stored at −80° C. until quantitation. Separate gels were made for each time point. BMP-2 was quantified using a sandwich ELISA. Rat posterolateral lumbar intertransverse spinal fusion: This study was approved by the Institutional Animal Care and Use Committee and was conducted in line with IACUC policies and procedures. One hundred and twelve female Sprague-Dawley rats at ages 12-16 weeks were utilized (Table 1). Control groups consisted of 0 μg BMP-2 per animal in collagen sponges (negative control), and 10 μg BMP-2 per animal in collagen sponges (positive control; fuses at a rate of 100% in this model). Animals were first assigned to one of three treatment groups: the diluted BMP-2-binding PA gels, the diluent PA gels, or the collagen sponge. Each treatment was further divided into sub-groups with varying BMP-2 doses of 0, 0.1, and 1 μg per animal, which have been shown previously not to reliably fuse the spine when applied on a collagen sponge in this model. In all conditions, the denoted BMP-2 dose refers to total growth factor dose implanted per animal. For instance, in the 1 μg BMP-2 treatment group, two biomaterials were each impregnated with 0.5 μg BMP-2 and implanted adjoining the L4-L5 transverse processes on either side of the spine. Each PA gel was prepared at 100 μL for each side of the spine. Surgical procedures: Rats were maintained on a heating pad under continuous anesthesia with an isoflurane inhalational anesthetic delivery system, and they were monitored by an assistant for cardiac or respiratory difficulties throughout the procedure. Utilizing a previously-described surgical technique, a posterior midline incision was made over the lumbar spinous processes, after which two separate fascial incisions were made 4 mm from the midline. The L4 and L5 transverse processes were exposed using a muscle-splitting approach via blunt dissection down to the periosteum. After adequate exposure, the fusion bed was irrigated with sterile gentamicin/saline solution, and a high-speed burr was used to decorticate the superficial cortical layer of the transverse processes. Graft materials were then implanted bilaterally in the paraspinal musculature between the transverse processes. The fascia and skin incisions were closed using a simple interrupted pattern with a 3-0 Monocryl absorbable suture, which was removed from the skin 7-10 days post-surgery. Following surgery, rats were housed in separate cages and allowed to eat, drink, and bear weight ad libitum.

Manual Palpation

Fusion was assessed via manual palpation following euthanasia at 8 weeks post-surgery. Spines were scored by three blinded observers using a previously established scoring system: 0=no bridging; 1=unilateral bridging; 2=bilateral bridging; and 3=bilateral bridging with abundant bone [39]. Spines that received an average score of 1.0 or greater were considered successfully fused.

Micro-Computed Tomography Analysis

Specimens deemed by manual palpation as successfully fused were subject to three-dimensional μCT analysis to compare the amount of new bone formed in the transverse processes, using a Skyscan 1172 Microtomograph System (Bruker MicroCT, Kontich, Belgium). In addition, 3 control specimens without a fusion mass were analyzed and averaged to determine the host bone volume. Two spines were placed in a plastic holder and scanned simultaneously with the spines' axes parallel to the rotation axis of the scanner. The microfocus x-ray tube was operated at 59 kVp and 167 μA, with an exposure time of 316 ms. MicroCT scans were performed with 34.5 μm isotropic volume elements (voxels), and a mean of 777 (range: 523-849) contiguous slice data sets encompassed the L4 and L5 transverse processes. Using ImageJ software analysis tools (NIH, Bethesda, Md.) the amount of newly formed bone was quantified between the L4 and L5 transverse processes utilizing axial images for each specimen. Regions of interest (ROI) were manually defined in each slice and included the two posterolateral intertransverse fusion beds of each spine. Within the ROI, voxels more absorbing than a pre-defined threshold were identified as bone. Total bone was then calculated by adding values for each image in the fusion bed. The threshold of 450 mg/cm3 was selected by examining several specimens and selecting the value best reproducing the structure of newly formed bone, as seen in the gray scale reconstructions. The host bone volume in the L4 and L5 transverse processes was quantified in the 3 control animals outside of the study groups and averaged (256±24 mm3). The volume of new bone formed for each spine was calculated by subtracting the mean host bone from total bone volume in each specimen.

Histology

After detachment of surrounding soft-tissue, spine specimens were fixed in 10% neutral-buffered formalin, decalcified in HCl/EDTA, and embedded in paraffin. Serial sagittal 5 μm cuts were made along the transverse processes of L4 and L5 and stained with hematoxylin and eosin.

Statistics and Data Analysis

For the in vitro cell culture study, data were analyzed using a one-way analysis of variance (ANOVA) with a Newman-Keuls multiple comparison post-hoc test. Statistical analysis was performed with the aid of Prism v5.0a. For spinal fusion study, manual palpation scores and microCT data were evaluated using a one-way ANOVA with a Levine's F test for equality of variances and independent t test for equality of means with the aid of SPSS. In all studies, statistical significance was accepted with P<0.05.

Fluorescence Spectroscopy

Critical micelle concentration measurements were performed using Nile Red fluorescence spectroscopy. For pH 7.5, PA samples were prepared in concentrations ranging from 100 nM to 1 mM, and Nile Red in ethanol (75 μM) was added to a final concentration of 250 nM. These samples were vortexed, sonicated, and were allowed to equilibrate for 24 hours before fluorescence spectra were obtained. For pH 8.5, PA samples were horn sonicated prior to the addition of Nile Red, and fluorescence spectra were obtained the same day.

Cell Cytotoxicity Assay

C2C12 cells were treated with 10 μg/mL heparin or PAs for 5 h (Day 0), and a fraction of the media was collected to measure the presence of lactate dehydrogenase (LDH), a cytosolic enzyme only released upon cell lysis, using Cyto-Tox 96 Non-Radioactive Cytotoxicity Assay (Promega, Madison, Wis.) (n=6). In addition, the remaining cells were stained for viable and dead cells using LIVE/DEAD Viability/Cytoxocity Kit (Invitrogen, Grand Island, N.Y.).

Mouse Ectopic Bone Formation

C57Bl/6 female mice, ages 6-12 weeks, were utilized for this study, which was approved by the Institutional Animal Care and Use Committee and was conducted in line with IACUC policies and procedures. The BMP-2-binding PA and the diluent PA were each reconstituted in water at 2 wt % and were mixed at the following ratios: 100% BMP-2-binding PA; 50% BMP-2-binding PA+50% diluent PA; and 10% BMP-2-binding PA+90% diluent PA. PA gels were assembled by mixing 20 μL of the PA solutions with 20 μL of 20 mM CaCl$_2$) containing 1 μg of BMP-2 at 20 min prior to surgical application of the gels. Mice were anesthetized with a continuous isoflurane inhalational anesthetic and monitored for cardiac or respiratory difficulties by an assistant throughout the procedure. A 2 cm incision was made on the posterolateral aspect of the left thigh. Graft materials were then implanted into the posterior compartment of the thigh. The muscle and skin incisions were closed using an interrupted pattern with a 4-0 monocryl absorbable suture, which was removed 10 days post-surgery. Mice were housed in separate cages and allowed to eat, drink, and bear weight ad libitum. Bone formation was assessed at 2 weeks post-surgery via radiographs.

Dorsal-Ventral X-Ray Radiograph for Spinal Fusion Study

Dorsal-ventral radiographs were taken under isoflurane anesthesia at 4 and 8 weeks post-surgery using a COMPAC5 anesthesia machine (Vetequip, Pleasanton, Calif.), with settings and specifications selected for the spine region: 4 cm thickness, 45 kvp, 3.2 mAs, 160 mA, and 0.040 s.

All publications and patents listed below and/or provided herein are hereby incorporated by reference in their entireties. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

REFERENCES

The following references, some of which are cited above, are herein incorporated by reference in their entireties.

W. K. Hsu, M. S. Nickoli, J. C. Wang, J. R. Lieberman, H. S. An, S. T. Yoon, J. A. Youssef, D. S. Brodke, C. M. McCullough, Global Spine J 2012, 02, 239.

B. Aghdasi, S. R. Montgomery, M. D. Daubs, J. C. Wang, Surgeon 2013, 11, 39.

W. Latham, J. T. C. Lau, Techniques in Orthopaedics 2011, 26, 14.

A. H. Reddi, Nature Biotechnology 1998, 16, 247.

R. S. Brower, N. M. Vickroy, Spine 2008, 33, E653.

R. D. Muchow, W. K. Hsu, P. A. Anderson, Spine J 2010, 10, el.

R. Vaidya, A. Sethi, S. Bartol, M. Jacobson, C. Coe, J. G. Craig, J Spinal Disord Tech 2008, 21, 557.

D. A. Wong, A. Kumar, S. Jatana, G. Ghiselli, K. Wong, The Spine Journal 2008, 8, 1011.

H. T. Aro, S. Govender, A. D. Patel, P. Hernigou, A. Perera de Gregorio, G. I. Popescu, J. D. Golden, J. Christensen, A. Valentin, J Bone Joint Surg Am 2011, 93, 801.

B. M. Willie, A. Petersen, K. Schmidt-Bleek, A. Cipitria, Soft Matter 2010.

W. K. Hsu, M. Polavarapu, R. Riaz, A. C. Larson, J. J. Diegmueller, J. H. Ghodasra, E. L. Hsu, Spine 2013, 38, E691.

K. Lee, E. A. Silva, D. J. Mooney, J R Soc Interface 2011, 8, 153.

N. J. Shah, M. N. Hyder, J. S. Moskowitz, M. A. Quadir, S. W. Morton, H. J. Seeherman, R. F. Padera, M. Spector, P. T. Hammond, Sci Transl Med 2013, 5, 191ra83.

D. S. W. Benoit, S. D. Collins, K. S. Anseth, Adv Funct Mater 2007, 17, 2085.

M. P. Lutolf, P. M. Gilbert, H. M. Blau, Nature 2009, 462, 433.

E. T. Pashuck, M. M. Stevens, Sci Transl Med 2012, 4, 160sr4.

G. A. Hudalla, W. L. Murphy, Adv Funct Mater 2011, 21, 1754.

J. Hartgerink, E. Beniash, S. Stupp, Science 2001, 294, 1684.

J. B. Matson, R. H. Zha, S. I. Stupp, Current Opinion in Solid State and Materials Science 2011, 15, 225.

V. Tysseling-Mattiace, V. Sahni, K. Niece, D. Birch, C. Czeisler, M. G. Fehlings, S. I. Stupp, J. A. Kessler, Journal of Neuroscience 2008, 28, 3814.

R. N. Shah, N. A. Shah, M. M. Del Rosario Lim, C. Hsieh, G. Nuber, S. I. Stupp, Proceedings of the National Academy of Sciences 2010, 107, 3293.

M. J. Webber, J. Tongers, C. J. Newcomb, K. T. Marquardt, J. Bauersachs, D. W. Losordo, S. I. Stupp, Proceedings of the National Academy of Sciences 2011, 108, 13438.

Z. Huang, C. J. Newcomb, P. Bringas, S. I. Stupp, M. L. Snead, Biomaterials 2010, 31, 9202.

A. Mata, Y. Geng, K. Henrikson, C. Aparicio, S. R. Stock, R. L. Satcher, S. I. Stupp, Biomaterials 2010, 31, 6004.

T. D. Sargeant, M. O. Guler, S. M. Oppenheimer, A. Mata, R. L. Satcher, D. C. Dunand, S. I. Stupp, Biomaterials 2008, 29, 161.

K. Rajangam, H. A. Behanna, M. J. Hui, X. Han, J. F. Hulvat, J. W. Lomasney, S. I. Stupp, Nano letters 2006, 6, 2086.

S. S. Lee, B. J. Huang, S. R. Kaltz, S. Sur, C. J. Newcomb, S. R. Stock, R. N. Shah, S. I. Stupp, Biomaterials 2012, 34, 452.

I. Capila, R. J. Linhardt, Angewandte Chemie (International ed in English) 2002, 41, 391.

M. R. Morgan, M. J. Humphries, M. D. Bass, Nat Rev Mol Cell Biol 2007, 8, 957.

K. Rajangam, M. S. Arnold, M. A. Rocco, S. I. Stupp, Biomaterials 2008, 29, 3298.

S. Ghanaati, M. Webber, R. Unger, C. Orth, J. F. Huvat, M. Barbeck, A. Rasic, S. I. Stupp, C. J. Kirkpatrick, Biomaterials 2009, 30, 6062.

H. A. Behanna, J. J. J. M. Donners, A. C. Gordon, S. I. Stupp, J Am Chem Soc 2005, 127, 1193.

E. T. Pashuck, H. Cui, S. I. Stupp, J Am Chem Soc 2010, 132, 6041.

J. Boekhoven, A. M. Brizard, P. van Rijn, M. C. A. Stuart, R. Eelkema, J. H. van Esch, Angewandte Chemie (International ed in English) 2011, 50, 12285.

S. Knecht, D. Ricklin, A. N. Eberle, B. Ernst, J. Mol. Recognit. 2009, 22, 270.

B. Zhao, T. Katagiri, H. Toyoda, T. Takada, T. Yanai, T. Fukuda, U.-I. Chung, T. Koike, K. Takaoka, R. Kamijo, J Biol Chem 2006, 281, 23246.

D. S. Bramono, S. Murali, B. Rai, L. Ling, W. T. Poh, Z. X. Lim, G. S. Stein, V. Nurcombe, A. J. van Wijnen, S. M. Cool, Bone 2011, 50, 954.

W. K. Hsu, J. C. Wang, N. Q. Liu, L. Krenek, P. A. Zuk, M. H. Hedrick, P. Benhaim, J. R. Lieberman, J Bone Joint Surg Am 2008, 90, 1043.

W. K. Hsu, M. Polavarapu, R. Riaz, G. C. Roc, S. R. Stock, Z. S. Glicksman, J. H. Ghodasra, E. L. Hsu, J Orthop Res 2011, 29, 1812.

W.-J. Kuo, M. A. Digman, A. D. Lander, Mol Biol Cell 2010, 21, 4028.

X. Jiao, P. C. Billings, M. P. O'Connell, F. S. Kaplan, E. M. Shore, D. L. Glaser, J Biol Chem 2007, 282, 1080.

H. Uludag, D. D'Augusta, J. Golden, J. Li, G. Timony, R. Riedel, J. M. Wozney, J Biomed Mater Res 2000, 50, 227.

M. Webber, J. Tongers, M. Renault, J. Roncalli, D. Losordo, S. Stupp, Acta biomaterialia 2010, 6, 3.

N. Angeloni, C. Bond, Y. Tang, D. A. Harrington, S. Zhang, S. I. Stupp, K. E. McKenna, C. A. Podlasek, Biomaterials 2010, 32, 1091.

S. Murali, B. Rai, C. Dombrowski, J. L. J. Lee, Z. X. H. Lim, D. S. Bramono, L. Ling, T. Bell, S. Hinkley, S. S. Nathan, J. H. Hui, H. K. Wong, V. Nurcombe, S. M. Cool, Biomaterials 2013, 34, 5594.

G. R. Bullock, P. Petrusz, Techniques in Immunocytochemistry, Academic Press, London [Etc.], 1982.

B. Peterson, P. G. Whang, R. Iglesias, J. C. Wang, J. R. Lieberman, J Bone Joint Surg Am 2004, 86-A, 2243.

The invention claimed is:

1. A method of promoting spinal fusion comprising administering to a subject in need thereof a gel composition comprising:
   (a) bone morphogenetic protein-2 (BMP-2); and
   (b) a BMP-2 binding peptide amphiphile comprising:
      (i) a hydrophobic non-peptidic segment;
      (ii) a β-sheet-forming peptide segment;
      (iii) an acidic peptide segment; and
      (iv) a BMP-2 binding peptide comprising the amino acid sequence of SEQ ID NO:1 (TSPHVPYGGGS);
   wherein the hydrophobic non-peptidic segment is covalently attached to the N-terminus of the β-sheet-forming peptide segment, wherein the C-terminus of the β-sheet-forming peptide segment is covalently attached to the N-terminus of the acidic peptide segment, and wherein the C-terminus of the acidic peptide segment is covalently attached to the N-terminus of the BMP-2 binding peptide, wherein the BMP-2 binding peptide amphiphile is diluted by about 50% in the composition with a diluent peptide amphiphile, wherein the diluent peptide amphiphile comprises a hydrophobic non-peptidic segment, a β-sheet forming segment, and an acidic peptide segment which matches the regions (i)-(iii) of the BMP-2 binding peptide amphiphiles, and wherein the diluent peptide amphiphile does not contain the amino acid sequence of SEQ ID NO:1.

2. The peptide amphiphile of claim 1, wherein the hydrophobic non-peptidic segment comprises an acyl chain.

3. The peptide amphiphile of claim 2, wherein the acyl chain comprises $C_6$-$C_{20}$.

4. The peptide amphiphile of claim 3, wherein the acyl chain comprises $C_{12}$ lauric acid.

5. The peptide amphiphile of claim 1, wherein the β-sheet-forming peptide segment comprises AAAVVV (SEQ ID NO:3).

6. The peptide amphiphile of claim 1, wherein the acid peptide segment comprise a Glu (E) and/or Asp (D) residue.

7. The peptide amphiphile of claim 6, wherein the acidic peptide segment comprises 2-7 amino acids in length wherein 50% or more amino acids are Glu (E) and/or Asp (D) residues.

8. The peptide amphiphile of claim 7, wherein the acidic peptide segment comprises EEE.

9. A method of promoting spinal fusion comprising administering to a subject in need thereof a gel composition comprising:
   (a) bone morphogenetic protein-2 (BMP-2); and
   (b) a BMP-2 binding peptide amphiphile comprising:
      (i) a hydrophobic non-peptidic segment;
      (ii) a β-sheet-forming peptide segment;
      (iii) an acidic peptide segment; and
      (iv) a BMP-2 binding peptide comprising the amino acid sequence of SEQ ID NO:1 (TSPHVPYGGGS);
   wherein the hydrophobic non-peptidic segment is covalently attached to the N-terminus of the β-sheet-forming peptide segment, wherein the C-terminus of the β-sheet-forming peptide segment is covalently attached to the N-terminus of the acidic peptide segment, and wherein the C-terminus of the acidic peptide segment is covalently attached to the N-terminus of the BMP-2 binding peptide, wherein the BMP-2 binding peptide amphiphile is diluted by about 50% in the composition with a diluent peptide amphiphile, wherein the diluent peptide amphiphile comprises a hydrophobic non-peptide segment which is an alkyl chain consisting of 6-20 carbons, an acidic peptide segment consisting of 2-7 amino acids in length wherein the amino acids are Glu and/or Asp and a β-sheet forming segment, and wherein the diluent peptide amphiphile does not contain the amino acid sequence of SEQ ID NO:1.

* * * * *